US010626407B2

(12) United States Patent
Li et al.

(10) Patent No.: US 10,626,407 B2
(45) Date of Patent: Apr. 21, 2020

(54) MATERIALS AND METHOD FOR MODIFYING A BIOCHEMICAL COMPONENT IN A PLANT

(71) Applicant: IOWA STATE UNIVERSITY RESEARCH FOUNDATION, INC., Ames, IA (US)

(72) Inventors: Ling Li, Mississippi State, MS (US); Eve Syrkin Wurtele, Ames, IA (US)

(73) Assignee: Iowa State University Research Foundation, Inc., Ames, IA (US)

(*) Notice: Subject to any disclaimer, the term of this patent is extended or adjusted under 35 U.S.C. 154(b) by 1 day.

(21) Appl. No.: 15/820,372

(22) Filed: Nov. 21, 2017

(65) Prior Publication Data

US 2018/0105826 A1    Apr. 19, 2018

Related U.S. Application Data

(60) Continuation of application No. 14/852,594, filed on Sep. 13, 2015, now Pat. No. 9,850,494, which is a division of application No. 13/314,139, filed on Dec. 7, 2011, now Pat. No. 9,157,091.

(60) Provisional application No. 61/446,460, filed on Feb. 24, 2011.

(51) Int. Cl.
  *C12N 15/82*   (2006.01)
  *A01H 5/10*    (2018.01)
  *C07K 14/415*  (2006.01)

(52) U.S. Cl.
  CPC .......... *C12N 15/8245* (2013.01); *A01H 5/10* (2013.01); *C07K 14/415* (2013.01); *C12N 15/8234* (2013.01); *C12N 15/8247* (2013.01); *C12N 15/8251* (2013.01); *C12N 2710/00043* (2013.01); *C12N 2830/008* (2013.01)

(58) Field of Classification Search
  None
  See application file for complete search history.

(56) References Cited

U.S. PATENT DOCUMENTS

| 5,792,920 A | 8/1998 | Bridges et al. |
| 2008/0113342 A1 | 5/2008 | Cao et al. |
| 2008/0184386 A1 | 7/2008 | Cao et al. |

OTHER PUBLICATIONS

Li et al. (Plant Journal, 58:485-498; 2009).*

(Continued)

*Primary Examiner* — Vinod Kumar
(74) *Attorney, Agent, or Firm* — Carol Larcher; Larcher & Chao Law Group

(57) ABSTRACT

A method of modifying the amount of at least one biochemical component in a plant comprising expressing Qua-Quine Starch (QQS) in the plant, the wild-type of which does not express QQS; a transgenic plant, or part thereof, which comprises and expresses QQS as a transgene and in which the amount of at least one biochemical component is modified; a tissue culture of regenerable cells of the transgenic plant; a vector comprising a nucleotide sequence, which encodes the coding sequence of QQS, operably linked to a non-native promoter, which promotes expression of the nucleotide sequence in a plant, which is other than *Arabidopsis*; and a method of producing a food or industrial product from a plant.

6 Claims, 3 Drawing Sheets

Specification includes a Sequence Listing.

(56) References Cited

OTHER PUBLICATIONS

Lin et al. (Planta, 225:153-164; 2006).*
Li et al. (Metabolic Engineering, 12:387-391; 2010), Bridges et al. (U.S. Pat. No. 5,792,920).*
Comai et al. (Plant Molecular Biology, 15:373-381; 1990).*
Müller-Röber et al. (EMBO Journal, 11:1229-1238; 1992).*
Comai et al., "Novel and useful properties of a chimeric plant promoter combining CaMV 35S and MAS elements," *Plant Molecular Biology*, 15: 373-381 (1990).
Li et al., "Chlamydomonas starch less mutant defective in ADP-glucose pyrophosphorylase hyper-accumulates triacylglycerol," *Metabolic Engineering*, 12: 387-391 (2010).
Li et al., "Identification of the novel protein QQS as a component of the starch metabolic network in *Arabidopsis* leaves," *Plant Journal*, 58(3): 485-498 (2009).
Li et al., "Uncovering Novel Signalling Interactions in Regulation of Plant Metabolic Networks," *Plant Biology*, Retrieved from the Internet: http://abstracts.aspb.org/pb2011/public/P14/P14009.html (2011).
Lin et al., "Genetic and transgenic perturbations of carbon reserve production in *Arabidopsis* seeds reveal metabolic interactions of biochemical pathways," *Planta*, 225: 153-164 (2006).

Muller-Rober et al., "Inhibition of the ADP-glucose pyrophosphorylase in transgenic potatoes leads to sugar-storing tubers and influences tuber formation and expression of tuber storage protein genes," *EMBO Journal*, 11: 1229-1238 (1992).
Seo et al., "Two splice variants of the IDD14 transcription factor competitively from nonfunctional heterodimers which may regulate starch metabolism," *Nature Comm.*, 2: 3-4 (2011).
Seo et al., "Two splice variants of the IDD14 transcription factor competitively from nonfunctional heterodimers which may regulate starch metabolism," *Nature Comm.*, 2:303, DOI: 10.1038 (2011).
Tanaka, "Flower Colour and cytochromes P450," *Phytochem Rev.*, 5: 283-291 (2006).
Wurtele et al., "ISURF Case #3844: High Protein Low Starch QQS Soybeans for Enhanced Value," *Iowa State Univ. Sci. & Tech.*, retrieved from the Internet: www.techtransfer.iastate.edu/documents/630141298651778854.pdf (2012).
Wurtele et al., "Starch-controlling gene fuels more protein in soybean plants," *Iowa State Univ. News Service*, retrieved from the Internet: www.news.iastate.edu/news/2011/apr/wurtele (2012).
Search Report & Written Opinion issued in Int'l App. No. PCT/US2011/063850 (dated 2012).

* cited by examiner

```
  1 ctcagaagaa gcctcctttc gatctgtcag ccattgaaga aacctccttt cgatctgtca
 61 gccattgaag atcagaagaa acaagactca cacggtcagc cattgaagaa gcctcctctc
121 attacctctc atcaaacatc tagatctgta cccaaacctt atccttttt ccttatttct
181 cgctttgtct attcttaatc tgattaatac ttgttgttgt tccaggttat agaagatctg
241 ggttgtgtta tatgcttcat tttctccaca gcgaccagtt ggtgtttggt tcttagattc
301 atgaagacca atagagagca ggaaatttac gttgaaagaa gcttcaaacc aaacaattca
361 acaattcaga atttgatgga cattgaaagg ttcattttgc ctcacacttc tacatcaggt
421 gtcgcaaggc tcaaaatgag ggtcatatca tgggtcgggc ttcagttcta caactactga
481 tattgggcct tatcacaaat tagttatagg gccattgtat ccaatattta atatctctgt
541 aaacttgttt aatggttatt ttgttctaat gcccattaca actaga [SEQ ID NO: 1]
```

FIG. 1a

MKTNREQEIYVERSFKPNNSTIQNLMDIERFILPHTSTSGVARLKMRVISWVGLQFYNY [SEQ ID NO: 2]

FIG. 1b

MATERIALS AND METHOD FOR MODIFYING A BIOCHEMICAL COMPONENT IN A PLANT

CROSS REFERENCE TO RELATED APPLICATIONS

This application is a continuation of co-pending U.S. patent application Ser. No. 14/852,594, filed Sep. 13, 2015, which is a divisional of co-pending patent application Ser. No. 13/314,139, filed Dec. 7, 2011, which claims priority to U.S. provisional application No. 61/446,460, filed Feb. 24, 2011, the contents of which are incorporated herein by reference in their entireties.

STATEMENT REGARDING FEDERALLY SPONSORED RESEARCH OR DEVELOPMENT

The invention disclosed herein was made with support from the Government of the United States of America under Grant Nos. MCB0209789 and MCB0951170 awarded by the National Science Foundation. The Government has certain rights in the invention.

TECHNICAL FIELD

This disclosure relates to materials and a method for modifying the amount of at least one biochemical component in a plant, in particular a crop plant. The amount of carbohydrate, e.g., starch, in leaves and/or seeds and the amount(s) of protein and/or lipid, e.g., oil, in seeds of plants can be modified in accordance with the present disclosure. Specifically, this disclosure relates to the expression of Qua-Quine Starch (QQS) in a plant (or a part thereof), in particular a crop plant, the WT of which does not otherwise express QQS.

BACKGROUND

Plant storage products include starch, lipid and protein. Different plant species differ in the kinds and relative proportions of storage products. Grain seeds, for example, comprise mainly starch, whereas oil seeds comprise mainly oil, and other seeds, such as soybean seeds, comprise mainly protein.

The pathways that produce starch, lipid and protein are connected by key intermediates. For example, hexoses, such as glucose, are precursors of starch synthesis and end products of starch degradation. Hexoses also can be converted to pyruvate, which can lead to (i) the production of acetyl-CoA and malonyl-CoA for fatty acid de novo synthesis, fatty acid elongation, polyketide formation, and isoprenoid synthesis and (ii) the biosynthesis of amino acids.

The ability to alter plant storage products, particularly for crop plants, has been a goal of plant breeders and those employing recombinant DNA techniques. Mike Rankin, a Crops and Soils Agent for the University of Wisconsin (UW), recently reported that Roger Borgers, a soybean specialist with UW has made a good case that low protein soybeans are costing the soybean industry as a whole due to discounted pricing for U.S. soybeans, which are comparatively low-protein, on the world market (World Wide Web at uwex.edu/ces/crops/SoyProtein.htm). According to those at the UW, soybeans from South America are valued more highly, and priced accordingly. Reportedly, one bushel of U.S. soybeans yields 21 pounds of protein and 11.4 pounds of oil, whereas Brazilian soybeans yield 24 pounds of protein and 13 pounds of oil. Rankin opines that more emphasis needs to be put on developing varieties with higher protein content, particularly given that there is a wide variation in soybean protein content within U.S. geographic regions (0.6-2.0%, depending on the year) and among varieties (32.3%-38.1% in Wisconsin). In this regard, the western Corn Belt and Wisconsin do not fare as well as other regions in the U.S., such as the southeast. Significant is that yield is not reduced with higher protein and oil content. In this regard, Baker et al. (Poultry Science 90: 390-395 (2011)) reported that soybean meal produced from high protein or low oligosaccharide varieties of soybeans have a greater nutritional value than soybean meal produced from conventional varieties of soybean and, therefore, could be fed in smaller amounts to broiler chickens.

Recently, the qua-quine starch (QQS) gene (locus ID At3g30720; GenBank Accession Nos. EU805808.1 and NM_113075.4) was found to have an effect on plant biochemical components in *Arabidopsis*. The QQS gene encodes a protein that contains 59 amino acids, has no known function, has no sequence similarity to other proteins in *Arabidopsis* or other organisms, has no known catalytic motifs, and no known structural motifs. Analysis of the QQS promoter indicates that it has a CCA1 binding site motif (AAAAATCT) at position −734, a TGA1 binding site motif (TGACGTGG; bZip transcription factor function) at position −504, an UPRMOTIFIAT motif (TGACGTGG; unfold protein response) at position −504, an ABRE-like binding site motif (GACGTGGC; ABA function) at position −503, and an ACGTABREMPTIFA2OSEM motif (ACGTGGC; ABA function) at position −502. QQS RNA transcripts increase during pollen development (from uninucleate microspores to bicellular pollen to tricellular pollen to mature pollen) in WT (WT) *Arabidopsis*, reaching peak levels in mature pollen. In wild type (WT) *Arabidopsis*, activity of the QQS promoter as determined using the β-glucuronidase (GUS) gene reporter system is evident at 2 days after imbibition (DAI) in hypocotyls and root tips. As seedlings grow, QQS expression expands to the vasculature, mesophyll cells, hydathodes, and trichomes of leaf blades and petioles. Microscopic dissection indicates no expression is detected in shoot meristem; the dark GUS staining in the shoot tip is associated with the adjacent vasculature. GUS activity is higher in mature leaves compared to young emerging leaves; it consistently appears somewhat unevenly distributed, and is predominantly located in the vasculature; this pattern is maintained throughout development. QQS expression is low in flower buds; however, by flower opening QQS expression is evident in pedicels, sepals, filaments, mature pollen, stigma papillae and styles, but not in petals. During silique development, QQS expression rises in the stigma papillae and style, and becomes apparent throughout the maternal tissues of the silique wall and receptacle. QQS is expressed in roots throughout development. Expression is highest in the root tip, specifically the root cap, columella cells and peripheral cap, and to a lesser extent in the root meristem region, but not in the epidermis. QQS is expressed at the site of lateral root initiation, and in the root tip and vasculature during its emergence; as the lateral root matures, expression remains detectable throughout the root cortex vasculature. GUS activity driven by the QQS promoter was higher in the Atss3 (starch synthase 3) single mutant than in WT under virtually all conditions. Expression was detectable throughout the entire seedling at 2 DAI, as well as later in development, in particular in leaves, flowers and roots. Although the general pattern of expression is similar in the Atss3 mutant and WT, QQS is expressed ectopically in petals in the Atss3 mutant. QQS RNA accumulates neither in the nucleus nor in the plastids. Expression of QQS promoter-GUS in the Atss2/Atss3 double-mutant background was more nuanced, but was in general similar to or somewhat lower than that in WT throughout leaf development. QQS transcripts increased seven-fold during the diurnal cycle in the Atss3 mutant compared to WT *Arabidopsis*; QQS protein levels also increased in the Atss3 mutant compared to WT *Arabidopsis*. Analysis of QQS RNAi (interfering RNA) mutants showed that starch content increased 20-30% at the end of the light cycle (about the same increase as observed in Atss3 mutants) due to increased starch biosynthesis and not decreased starch degradation; there was no difference in starch content at the end of the dark cycle. Starch content decreased to WT level within four hours of the dark cycle. All of the above examples are described in Li et al., Plant Journal 58: 485-498 (2009).

In view of the foregoing, it is an object of the present disclosure to provide materials and a method of modifying the amount of at least one biochemical component in a plant. This and other objects and advantages, as well as inventive features, will become apparent from the detailed description provided herein.

SUMMARY

A method of modifying the amount of at least one biochemical component in a plant is provided. The method comprises expressing Qua-Quine Starch (QQS) in a plant, the WT of which does not express QQS, in an amount that modifies the amount of at least one biochemical component in the plant. The biochemical component can be protein, lipid (e.g., oil), polyketide, isoprenoid, and/or carbohydrate (e.g., starch). When the biochemical component is protein, the amount of protein in the seeds of the plant expressing QQS can be increased compared to the amount of protein in the seeds of the WT plant. When the biochemical component is oil, the amount of oil in the seeds of the plant expressing QQS can be decreased compared to the amount of oil in the seeds of the WT plant. When the biochemical component is starch, the amount of starch in the leaves of the plant expressing QQS can be decreased compared to the amount of starch in the leaves of the WT plant.

When the plant is soybean and the biochemical component is protein, the amount of protein in the seeds of the soybean can be increased by at least about 30% as compared to the amount of protein in the seeds of WT soybean. The amount of protein in the seeds of the soybean can be increased by at least about 45%, such as by at least about 60%.

In view of the above, also provided is a transgenic plant, or part thereof, which comprises and expresses QQS as a transgene. In the transgenic plant, or part thereof, at least one biochemical component is present in an amount that differs from the amount present in a corresponding WT plant, or part thereof, which does not express QQS. The transgenic plant, or part thereof, can be soybean.

Also in view of the above, a tissue culture of regenerable cells of a transgenic plant (or part thereof), which comprises and expresses QQS as a transgene, is provided. At least one biochemical component is present in the transgenic plant in an amount that differs from the amount present in a corresponding WT plant, or part thereof, which does not express QQS.

A vector is further provided. The vector comprises a nucleotide sequence, which encodes the coding sequence of QQS, operably linked to a non-native promoter, which promotes expression of the amino acid sequence of the nucleotide sequence in a plant, wherein the plant is other than *Arabidopsis*. The nucleotide sequence preferably encodes the amino acid sequence of SEQ ID NO: 2. An example of such a nucleotide sequence is SEQ ID NO: 1. The promoter can be any suitable promoter, such as a constitutive promoter, e.g., a Cauliflower mosaic virus 35S promoter, an inducible promoter, a developmentally specific promoter, such as a seed-specific promoter, or a synthetic promoter, e.g., a hybrid promoter.

A method of producing a food or industrial product from a plant is still further provided. The method comprises preparing the food or industrial product from a cultivated transgenic plant or a cultivated plant regenerated from a tissue culture of regenerable cells of a transgenic plant (or part thereof). The transgenic plant comprises and expresses QQS as a transgene. At least one biochemical component is present in the transgenic plant in an amount that differs from the amount present in a corresponding WT plant, or part thereof, which does not express QQS. While the transgenic plant, or part thereof, can be any plant in which the modification of the amount of a biochemical component is desired (as indicated above), a preferred plant is soybean.

BRIEF DESCRIPTION OF FIGURES

FIG. 1*a* is the nucleotide sequence of the *Arabidopsis thaliana* Qua-Quine Starch (QQS) cDNA [SEQ ID NO: 1].

FIG. 1*b* is the amino acid sequence of the *Arabidopsis thaliana* QQS protein [SEQ ID NO: 2].

DETAILED DESCRIPTION

Figure 2:
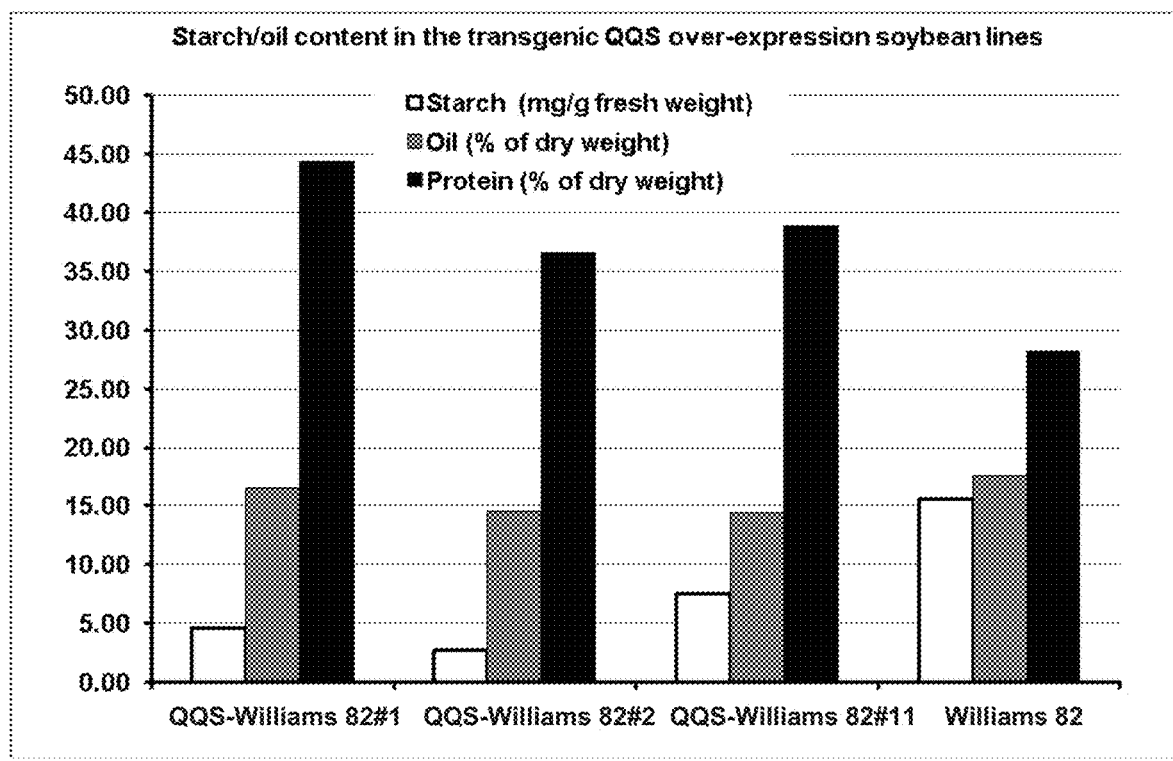
FIG. 2 is a bar graph of starch content (mg/g fresh weight), oil (% dry weight), and protein (% dry weight) in transgenic soybean lines vs. WT (Williams 82) soybean.

The present disclosure is predicated, at least in part, on the surprising and unexpected discovery that the qua-quine starch (QQS) gene (locus tag At3g30720; GenBank Accession Nos. EU805808.1 and NM_113075.4), which encodes a protein that contains 59 amino acids, has an effect on biochemical components in *Arabidopsis*, has no sequence similarity to other proteins in *Arabidopsis* or other organisms, has no known catalytic motifs, and no known structural motifs, also has an effect on biochemical components in other plants. The ability to modify the amount of at least one biochemical component in a plant by expressing QQS in the plant enables the generation of plant lines with more desirable biochemical component compositions without conducting extensive breeding studies.

In view of the above, a method of modifying the amount of at least one biochemical component in a plant is provided. The method comprises expressing QQS in the plant, the WT of which does not express QQS, in an amount (i.e., an effective amount, e.g., a biochemical component-modifying amount), or at a level (i.e., an effective level, e.g., a biochemical component-modifying level), that modifies the amount of at least one biochemical component in the plant. When QQS is expressed in the plant (the wild-type of which does not express QQS) and the amount of at least one biochemical component in the plant is modified, QQS is being expressed in the plant in an amount, or at a level, that modifies the amount of at least one biochemical component in the plant. The method can be used to produce a food product (or a component or an ingredient thereof) for human consumption, feed (or a component or an ingredient thereof) for non-human animal consumption, or an industrial product (i.e., any and all non-food products, or components or ingredients thereof), such as in accordance with methods described herein. In this regard, the "biochemical component," as described herein below, e.g., a biochemical component, which is increased in amount, or a plant (or part thereof), in which a biochemical component is increased/decreased in amount, can be the food product (or a component or an ingredient thereof), the feed (or a component or an ingredient thereof), or the industrial product (or a component or an ingredient thereof).

By "biochemical component" is meant any fraction of the composition of a plant (e.g., carbon fraction, nitrogen fraction, phosphorus fraction, or ion fraction), any class of compounds/ions of which a fraction is comprised (e.g., polysaccharides, sugars, organic acids, phenolics, tannins, hemicelluloses, lipids, terpenoids, cellulose and lignin of the carbon fraction; protein, amino acid, alkaloid, nitrate and nucleic acid of the nitrogen fraction; phosphate, polyphosphate, phospholipid, nucleic acid, and sugar phosphate of the phosphorus fraction; and potassium, calcium, magnesium, salt, and heavy metal of the ion fraction), and any compound of which a class of compounds is comprised that is built-up in a plant and can be mobilized to support biosynthesis for growth or other plant functions (see, e.g., Chapin, III et al., Ann. Rev. of Ecology and Systematics 21: 423-447 (1990) and references cited therein, all of which are hereby incorporated by reference in their entireties). Examples of plant lipid classes include neutral lipids, such as triacylglycerol, diacylglycerol, and monoacylglycerol, and polar lipids, such as monogalactosyldiacylglycerol, digalactosyldiacylglycerol, phosphatidylglycerol, phosphatidylcholine, phosphatidylethanolamine, phosphatidylinositol, phsophatidylserine, and sulfoquinovosyldiacylglycerol. Common plant fatty acids include palmitic acid, palmitoleic acid, palmitolenic acid, stearic acid, oleic acid, linoleic acid, linolenic acid, arachidic acid, eicosenoic acid, eicosadienoic acid, and erucic acid. A "biochemical component" is intended to encompass a compound that can be formed by one or more types of storage processes (e.g., starch and amino acids) and a compound that can serve a storage role and a non-storage role (e.g., ribulose bis-phosphate carboxylase (RUBISCO) and tannins). The biochemical component can be protein, lipid (e.g., oil), polyketide, isoprenoid, and/or carbohydrate (e.g., starch).

By "modifying" is meant increasing or decreasing the amount of a biochemical component. In this regard, the expression of QQS in the plant can modify one or more biochemical components by increasing the amount of one or more biochemical components, decreasing the amount of one or more biochemical components, or simultaneously increasing the amount of one or more biochemical components and decreasing the amount of one or more other biochemical components. Thus, the biochemical component can be protein, and the amount of protein in the seeds, for example, of the plant expressing QQS can be increased compared to the amount of protein in the seeds of the WT plant. Additionally or alternatively, the biochemical component can be lipid (e.g., oil), and the amount of lipid (e.g., oil) in the seeds, for example, of the plant expressing QQS can be decreased compared to the amount of lipid (e.g., oil) in the seeds of the WT plant. Also, additionally or alternatively, the biochemical component can be carbohydrate (e.g., starch), and the amount of carbohydrate (e.g., starch) in the leaves, seeds, or leaves and seeds, for example, of the plant expressing QQS can be decreased compared to the amount of carbohydrate (e.g., starch) in the leaves, seeds, or leaves and seeds, respectively, of the WT plant. The amount of at least one biochemical component can be modified, such as by increasing or decreasing, by at least about 5%, 10%, 15%, 20%, 25%, 30%, 35%, 40%, 45%, 50%, 55%, 60%, 65%, 70%, 75%, 80%, 85%, 90%, 95% or more. For example, as demonstrated herein, when the plant is soybean and the biochemical component is protein, the amount of protein in the seeds of the soybean can be increased by at least about 30%, such as 32.63% (based on dry weight), at least about 45%, such as 47.08% (based on dry weight), at least about 60%, such as 60.63% (based on dry weight), or more.

When the amount of at least one biochemical component is modified by increasing the amount of the biochemical component, it can be preferable and even desirable to supplement the growing conditions of the plant, such as soil or other media in which the plant is grown, with a composition that provides one or more nutrients essential to the growth of the plant and/or the increased production of at least one biochemical component in the plant. The composition can be inorganic (e.g., mineral), organic (e.g., derived from a plant and/or animal), or a combination thereof. The composition can be of natural origin, synthetic origin, or a combination thereof. An example of such a composition is a fertilizer (e.g., Miracle Gro Excel 15-5-15). A fertilizer typically provides, in varying proportions, macronutrients, such as nitrogen, phosphorus, potassium, calcium, magnesium, and sulfur. A fertilizer also typically provides, in varying proportions, micronutrients, such as boron, chlorine, copper, iron, manganese, molybdenum, and zinc. Other nutrients, such as carbon, hydrogen, and oxygen, are typically supplied by water and carbon dioxide. If desired, the composition (e.g., fertilizer) can be a controlled-release composition. In this regard, the components of the controlled-release composition can be released at the same rate or at different rates and/or in the same amounts or in different amounts. An excess amount of a given biochemical component can be released from a plant, which expresses a biochemical-component modifying amount/level of QQS, into its environment as part of the plant's normal growth/development or life cycle.

The plant can be any plant in which the modification of the amount of a biochemical component is desired. For example, the plant can be a monocot, a dicot, or a fungus. Examples of plants include agriculturally important plants, such as cereal crops, industrial plants, legumes, fruits, vegetables, root plants, turf grasses, woody plants, tropical plants, nuts, ornamental plants, medicinal plants, and fungi, among others, and, more specifically, corn, soybean, wheat, barley, oat, flax, kiwicha, bulgur, quinoa, millet, sorghum, sugarcane, potato, sweet potato, cotton, rice (e.g., indica and japonica), rye, canola, oilseed rape, sunflower, tobacco, beans, alfalfa, Bermudagrass, perennial ryegrass, switchgrass, tall fescue, turf grasses, American elm, American chestnut, cork oak tree, eucalyptus, pine, poplar, rubber tree, banana, blackberry, blueberry, strawberry, raspberry, cantaloupe, melon, cucumber, eggplant, tomato, lettuce, radish, mushroom, carrot, cassava, onion, lentil, pea, chickpea, pigeonpea, cowpea, red clover, bean, lima bean, kidney bean, broad bean, velvet bean, tepary bean, pepper, broccoli, spinach, squash, pumpkin, mustard, mustard greens, Indian mustard, apple, pear, peach, cherry, plum, grape, cabbage, cauliflower, brussel sprouts, citrus, orange, lemon, lime, grapefruit, tangerine, clementine, pomegranate, kiwi, starfruit, anise, papaya, pineapple, coffee, groundnut, palm kernel, walnut, peanut, almond, pecans, chestnuts, macadamia nuts, hazelnuts, sunflower, endive, leek, beet, turnip, clover, red clover, barrel clover, carnation, chrysanthemum, orchids, petunia, rose, ginseng, hemp, opium poppy, African locust bean, African oil bean, tarwi, tamarind, Mung bean, Sesban bean, Lablab bean, Jack-bean, lupin, and milkweed.

QQS can be expressed in the plant using any suitable method as is known in the art. For example, QQS can be introduced into the plant as a transgene using electroporation, microprojectile bombardment, *Agrobacterium*-mediated transformation (as exemplified herein in Example 1), and direct contact of protoplasts. Transformation/transfection (as well as other techniques used to introduce DNA into a plant or fungus) and regeneration of monocots and dicots is a matter of routine. The particular method employed will depend, in part, on the type of plant or fungus to be transformed/transfected. For example, numerous protocols are described in *Agrobacterium* Protocols, 2$^{nd}$ ed., Vols. 1 and 2, Methods in Molecular Biology, which was edited by Kan Wang and published by Humana Press, Totowa, N.J., and which is specifically incorporated herein by reference in its entirety. Such protocols include the floral dip transformation method and methods of transforming leaf explants, cotyledon explants, and root explants, as well as specific protocols for transformation of barrel clover, tobacco, barley, corn, rice (indica and japonica), rye, sorghum, wheat, canola, cotton, Indian mustard, sunflower, alfalfa, chickpea, clover, pea, peanut, pigeonpea, red clover, soybean, tepary bean, taro, cabbage, cucumber, eggplant, lettuce, tomato, carrot, cassava, potato, sweet potato, yam, Bermudagrass, perennial ryegrass, switchgrass, tall fescue, turf grasses, American elm, cork oak, eucalyptus tree, pine, poplar, rubber tree, banana, citrus, coffee, papaya, pineapple, sugarcane, American chestnut, apple, blueberry, grapevine, strawberry, walnut, carnation, chrysanthemum, orchids, petunia, rose, ginseng, hemp, opium poppy, and mushroom. Other methods of *Agrobacterium*-mediated transformation of cereals are described by Shrawat et al., Plant Biotech. J. 4(6): 575-603 (November 2006), which is specifically incorporated herein by reference in its entirety. Other methods of transformation of legumes are described by Somers et al., Plant Physiol. 131(3): 892-899 (March 2003), which is specifically incorporated herein by reference in its entirety. Methods useful for the transformation of rice are described by Giri et al., Biotech. Adv. 18(8): 653-683 (December 2000), and Hiei et al., Plant Mol. Biol. 35(1-2): 205-218 (September 1997), both of which are specifically incorporated herein by reference in their entireties. Vasil et al., Methods Molec. Biol. 111: 349-358 (1999), and Jones et al., Plant Methods 1(1): 5 (Sep. 5, 2005), both of which are specifically incorporated herein by reference in their entireties, describe methods useful for the transformation of wheat. The use of direct DNA uptake in barley has been described by Lazzeri, Methods Molec. Biol. 49: 95-106 (1996), which is specifically incorporated herein by reference in its entirety. The use of temporary immersion in a bioreactor system to transform strawberries is described by Hanhineva et al., BMC Biotech. 7: 11 (2007), which is specifically incorporated herein by reference in its entirety. The introduction of transgenes into plastids, such as chloroplasts, specifically chloroplasts in tobacco, has been described by Daniell et al., Trends Biotech. 23(5): 238-245 (May 2005), which is specifically incorporated herein by reference in its entirety. In this regard, Lutz et al., Plant Physiol. 145(4): 1201-1210 (2007) (specifically incorporated herein by reference in its entirety), provides guidance in the selection of vectors for transformation of the plastid genome in higher plants. Somatic embryogenesis of species-specific chloroplast vectors also has application in plants, such as soybean, carrot, and cotton, for example. Other methods useful for the transformation of beets have been described by Golovko et al., Tsitol. Genet. 39(3): 30-36 (May-June 2005), which is specifically incorporated herein by reference in its entirety.

A nucleotide sequence, which encodes the coding domain sequence (CDS) of QQS, can be incorporated into a vector or a cassette (collectively referred to herein as vectors) for expression in a plant. Numerous expression vectors suitable for stable transformation of plant cells or for the establishment of transgenic plants have been described (see, e.g., Weissbach et al., Methods for Plant Molecular Biology, Academic Press, New York, N.Y. (1989); and Gelvin et al., Plant Molecular Biology Manual, Kluwer Academic Publishers, Norwell, Mass. (1990)). The Ti plasmid from *Agrobacterium tumefaciens* or a binary *Agrobacterium* vector (Bevan, Nucl. Acids Res. 12: 8711-8721 (1984)) can be used to transform monocots and dicots. Non-Ti vectors, such as viral vectors, can be used to transfer DNA into plant cells, tissues, embryos, and plants. Non-Ti vectors can be introduced through the use of liposome-mediated transformation, polyethylene glycol (PEG)-mediated transformation, viral transfection, micro-injection, vacuum infiltration, electroporation of plant protoplasts, microprojectile bombardment, silicon carbide wiskers, and the like. See, e.g., Ammirato et al., Handbook of Plant Cell Culture—Crop Species, MacMillan Pub. Co. (1984); Shimamoto et al., Nature 338: 274-276 (1989); Fromm et al., Bio/Technology 8: 833-839 (1990); and Vasil et al., Biol. Technology 8: 429-434 (1990).

In addition to a coding sequence, a plant transformation/transfection vector comprises one or more 5' and 3' transcriptional regulatory sequences. Transcriptional regulatory sequences can include a promoter, a transcription initiation site, a transcription termination site, a polyadenylation signal, and a 3' terminator region (e.g., PI-II terminator region of potato, octopine synthase 3' terminator region, or nopaline synthase 3' terminator region). If a conventional, nuclear processed intron is present, one or more RNA processing signals, such as intron splice sites, also can be included. Any suitable promoter can be used. In this regard, the QQS promoter can be used. Alternatively, a non-QQS promoter can be used. The promoter can be constitutive, synthetic (e.g., hybrid), inducible, developmentally regulated, environmentally regulated, hormonally regulated, chemically regulated, cell-specific, or tissue-specific (e.g., seed-specific), for example. Constitutive promoters include the cauliflower mosaic virus (CaMV) 35S promoter, the nopaline synthase promoter, and the octopine synthase promoter. Environmentally regulated, inducible promoters include promoters that are induced by light, for example. The napin promoter, the phaseolin promoter, and the DC3 promoter are examples of seed-specific promoters, whereas the dru1 promoter, the 2A11 promoter, and the tomato polygalacturonase promoter are examples of fruit-specific promoters, and PTA29, PTA26, and PTA13 are examples of pollen-specific promoters. The pBAN promoter is a seed coat promoter in

*Arabidopsis*, whereas p26, p63, and p63tr are early seed promoters from *Arabidopsis* (see, e.g., U.S. Pat. App. Pub. No. 2009/0031450). Examples of root-specific promoters are described in U.S. Pat. Nos. 5,618,988; 5,837,848; and 5,905,186. Other promoters are induced by auxin, cytokinin, gibberellin, methyl jasmonate, salicylic acid, heat, light, and the like.

In view of the above, a vector comprising a nucleotide sequence, which encodes the coding sequence of QQS, operably linked to a non-native promoter, which promotes expression of the nucleotide sequence in a plant, wherein the plant is other than *Arabidopsis*, is also provided. The nucleotide sequence preferably encodes the amino acid sequence of SEQ ID NO: 2. An example of such a nucleotide sequence is SEQ ID NO: 1, although one of ordinary skill in the art will appreciate that, due to the degeneracy of the genetic code, numerous other nucleotide sequences can encode the amino acid sequence of SEQ ID NO: 2. In this regard, one of ordinary skill in the art will also appreciate that one or more mutations can be introduced into the nucleotide sequence, thereby leading to changes in the amino acid sequence of QQS. If a mutation is introduced into the amino acid sequence of QQS, preferably the mutation does not alter the function of QQS or it improves the function of QQS in some way. By "non-native" is meant that the promoter is other than that which promotes the expression of QQS in WT *Arabidopsis*. "Non-native" is intended to encompass the use of other *Arabidopsis* promoters, i.e., other non-QQS promoters. As indicated above, the promoter can be any suitable promoter, such as a constitutive promoter, e.g., the cauliflower mosaic virus 35S promoter, a synthetic promoter (e.g., hybrid), an inducible promoter, a developmentally specific promoter, e.g., a seed-specific promoter, and a synthetic promoter, e.g., a hybrid promoter. Promoters that are highly active in soybean, e.g., a constitutive polyubiquitin promoter and an early embryo-specific heat shock protein 90-like promoter, are described in U.S. Pat. App. Pub. No. 2010/0186119. The method of modifying the amount of at least one biochemical component in a plant described herein is not limited to the use of a vector comprising a nucleotide sequence encoding the coding sequence of QQS operably linked to a non-native promoter; a vector comprising a nucleotide sequence encoding the coding sequence of QQS operably linked to the QQS promoter also can be used.

Following transformation/transfection (or other such methods of introducing DNA into a plant), plants can be selected using a dominant selectable marker (e.g., antibiotic or herbicide resistance) incorporated into the vector/cassette. After transformed/transfected plants are selected, they are grown to maturity. Plants showing a modified amount of at least one biochemical component are identified. Modulation can be confirmed through analysis of mRNA expression using Northern blots, RT-PCR, micro-arrays, or next generation sequencing, or through analysis of protein expression/accumulation using immunoblots, Western blots, or gel shift assays.

In view of the above, a transgenic plant, or part thereof, is also provided. The transgenic plant, or part thereof, comprises and expresses QQS as a transgene and at least one biochemical component is present in an amount that differs from the amount present in a corresponding WT plant, or part thereof, which does not express QQS. By "part thereof" is mean any part of a plant such as, but not limited to, root, stem, leaf, flower, stamen, pollen, pistil, seed, and the like. The transgenic plant can be any plant as indicated above, such as, but not limited to, soybean.

Also provided is a tissue culture of regenerable cells of the transgenic plant. By "tissue culture" is meant a composition comprising isolated cells, which can be the same or different, or a collection of such cells organized into one or more parts of a plant. Exemplary types of tissue cultures include an explant, a callus, an embryo, and a plantlet. By "regenerable" is meant that the cells can regenerate a plant like the transgenic plant from which the tissue culture was derived. Plant tissue culture techniques are known in the art (see, for example, Smith, *Plant Tissue Culture: Techniques and Experiments*, 2nd. ed., Academic Press (2000); and *Plant Tissue Culture, Development, and Biotechnology*, Trigiano and Gray, eds., CRC Press (2010), both of which are incorporated by reference in their entireties) and exemplified herein (see Example 2).

A method of producing a food or industrial product is also provided. "Food" includes food (or a component or an ingredient thereof) for human consumption as well as feed (or a component or an ingredient thereof) for non-human animal consumption. "Industrial" includes any and all non-food products (or components or ingredients thereof). The method can comprise preparing the food product (or a component or an ingredient thereof) or the industrial product (or a component or an ingredient thereof) from a cultivated transgenic plant as described above, e.g., soybean, or a cultivated plant regenerated from a tissue culture as described above. Thus, the present disclosure provides an improved method of producing a food product or an industrial product, wherein the improvement comprises preparing the food product or the industrial product from a cultivated transgenic plant or a cultivated plant regenerated from a tissue culture as described above.

Soybeans, for example, can be used in their entireties but are commonly processed into two primary products, i.e., soybean protein (meal) and crude soybean oil. Both of these products are commonly further refined for particular uses. The crude soybean oil can be broken down into glycerol, fatty acids, and sterols. The soybean protein can be divided into soy flour concentrates and isolates. Examples of "food" products made from soybean include, but are not limited to, coffee creamers, margarine, mayonnaise, salad dressings, shortenings, bakery products, chocolate coatings, cereal, beer, aquaculture feed, bee feed, calf feed replacers, fish feed, livestock feed, poultry feed, and pet feed. Examples of "industrial" products include, but are not limited to, binders, wood composites, anti-static agents, caulking compounds, solvents, disinfectants, fungicides, inks, paints, protective coatings, wallboard, anti-foam agents, and rubber.

If desired, the plants described herein can be used in plant breeding methods. For example, plant breeding methods can be used to introduce one or more other traits, e.g., higher yield, into the plants described herein. See, for example, the methods described in U.S. Pat. App. Pub. No. 2004/0060082, which published Mar. 25, 2004, and is hereby incorporated by reference in its entirety.

The methods described herein can be used to assess other proteins with obscure features (POF) in plants. Desirably, the POF shares certain characteristics with QQS, such as no sequence similarity to other proteins within the same plant, or no sequence similarity to other proteins in other plant species, such as related plant species within the same family, no known catalytic motifs, and no known structural motifs. Initially, the POF can be identified by comparing its primary amino acid sequence to other amino acid sequences in databases, such as PFAM, TIGRFAM, SMART, and Superfamily, using a statistical model of a consensus sequence for a group of homologous and/or orthologous polypeptides, such as a Hidden Markov Model (HMM) (see, e.g., Durbin et al., *Biological Sequence Analysis Probabilistic Models of Proteins and Nucleic Acids*, Cambridge University Press, Cambridge, UK (1988)), and finding no matches (Gollery et al., Genome Biol. 7: R57 (2006)). Examples of POFs identified in *Arabidopsis* by this method include: Locus ID AT1G01110, AT1G01130, AT1G01240, AT1G01400, AT1G01440, AT1G01500, AT1G01550, AT1G01725, AT1G01730, AT1G01810, AT1G01840, AT1G01990, AT1G02070, AT1G02110, AT1G02290, AT1G02320, AT1G02350, AT1G02380, AT1G02405, AT1G02450, AT1G02490, AT1G02540, AT1G02570, AT1G02700, AT1G02710, AT1G02870, AT1G02960, AT1G02965, AT1G02990, AT1G03055, AT1G03080, AT1G03090, AT1G03106, AT1G03170, AT1G03180, AT1G03200, AT1G03240, AT1G03260, AT1G03290, AT1G03320, AT1G03340, AT1G03420, AT1G03600, AT1G03660, AT1G03730, AT1G03780, AT1G03820, AT1G03910, AT1G04000, AT1G04030, AT1G04070, AT1G04200, AT1G04230, AT1G04330, AT1G04650, AT1G04660, AT1G04670, AT1G04750, AT1G04800, AT1G04930, AT1G04985, AT1G05040, AT1G05060, AT1G05065, AT1G05085, AT1G05090, AT1G05205, AT1G05210, AT1G05220, AT1G05320, AT1G05330, AT1G05340, AT1G05360, AT1G05385, AT1G05420, AT1G05430, AT1G05440, AT1G05450, AT1G05490, AT1G05575, AT1G05720, AT1G05780, AT1G05860, AT1G05894, AT1G06010, AT1G06135, AT1G06225, AT1G06240, AT1G06320, AT1G06420, AT1G06475, AT1G06500, AT1G06510, AT1G06540, AT1G06660, AT1G06770, AT1G06920, AT1G06923, AT1G06930, AT1G06950, AT1G06980, AT1G07020, AT1G07040, AT1G07060, AT1G07090, AT1G07135, AT1G07190, AT1G07290, AT1G07300, AT1G07330, AT1G07473, AT1G07476, AT1G07500, AT1G07680, AT1G07690, AT1G07795, AT1G07860, AT1G07910, AT1G07970, AT1G07985, AT1G07990, AT1G08020, AT1G08030, AT1G08035, AT1G08060, AT1G08180, AT1G08300, AT1G08380, AT1G08480, AT1G08520, AT1G08530, AT1G08580, AT1G09415, AT1G09470, AT1G09483, AT1G09645, AT1G09812, AT1G09950, AT1G09995, AT1G10100, AT1G10140, AT1G10155, AT1G10170, AT1G10180, AT1G10220, AT1G10250, AT1G10380, AT1G10385, AT1G10417, AT1G10420, AT1G10522, AT1G10530, AT1G10620, AT1G10650, AT1G10660, AT1G10690, AT1G10710, AT1G10790, AT1G10800, AT1G10840, AT1G10990, AT1G11070, AT1G11120, AT1G11240, AT1G11320, AT1G11400, AT1G11430, AT1G11440, AT1G11470, AT1G11480, AT1G11520, AT1G11655, AT1G11690, AT1G11850, AT1G11905, AT1G11915, AT1G12020, AT1G12040, AT1G12064, AT1G12080, AT1G12330, AT1G12380, AT1G12450, AT1G12530, AT1G12660, AT1G12670, AT1G12805, AT1G12810, AT1G12830, AT1G12845, AT1G13030, AT1G13220, AT1G13360, AT1G13390, AT1G13605, AT1G13607, AT1G13608, AT1G13609, AT1G13620, AT1G13650, AT1G13670, AT1G13755, AT1G13930, AT1G13990, AT1G14180, AT1G14280, AT1G14345, AT1G14450, AT1G14620, AT1G14630, AT1G14710, AT1G14755, AT1G14990, AT1G15010, AT1G15215, AT1G15230, AT1G15260, AT1G15270, AT1G15280, AT1G15320, AT1G15350, AT1G15385, AT1G15400, AT1G15415, AT1G15590, AT1G15600, AT1G15610, AT1G15620, AT1G15630, AT1G15640, AT1G15757, AT1G15770, AT1G15800, AT1G15825, AT1G15830, AT1G15840, AT1G15900, AT1G15940, AT1G16000, AT1G16020, AT1G16025, AT1G16080, AT1G16170, AT1G16500, AT1G16515, AT1G16630, AT1G16690, AT1G16730, AT1G16770, AT1G16790, AT1G16810, AT1G16840, AT1G16850, AT1G16860, AT1G16910, AT1G16950, AT1G16960, AT1G17030, AT1G17080, AT1G17090, AT1G17140, AT1G17270, AT1G17285, AT1G17300, AT1G17345, AT1G17350, AT1G17360, AT1G17400, AT1G17490, AT1G17510, AT1G17665, AT1G17780, AT1G17870, AT1G17900, AT1G17940, AT1G18000, AT1G18010, AT1G18060, AT1G18190, AT1G18220, AT1G18290, AT1G18380, AT1G18470, AT1G18510, AT1G18620, AT1G18730, AT1G18750, AT1G18810, AT1G18840, AT1G18850, AT1G18950, AT1G19010, AT1G19020, AT1G19030, AT1G19240, AT1G19330, AT1G19360, AT1G19394, AT1G19397, AT1G19400, AT1G19500, AT1G19520, AT1G19530, AT1G19620, AT1G19960, AT1G19980, AT1G19990, AT1G20070, AT1G20100, AT1G20180, AT1G20280, AT1G20290, AT1G20310, AT1G20430, AT1G20460, AT1G20530, AT1G20640, AT1G20690, AT1G20770, AT1G20830, AT1G20890, AT1G20970, AT1G21010, AT1G21020, AT1G21050, AT1G21170, AT1G21323, AT1G21330, AT1G21360, AT1G21370, AT1G21390, AT1G21395, AT1G21475, AT1G21500, AT1G21510, AT1G21520, AT1G21560, AT1G21580, AT1G21600, AT1G21610, AT1G21695, AT1G21740, AT1G21770, AT1G21830, AT1G21840, AT1G21940, AT1G21950, AT1G22010, AT1G22030, AT1G22060, AT1G22110, AT1G22120, AT1G22140, AT1G22230, AT1G22260, AT1G22275, AT1G22335, AT1G22420, AT1G22470, AT1G22590, AT1G22600, AT1G22680, AT1G22770, AT1G22790, AT1G22850, AT1G22885, AT1G22890, AT1G22970, AT1G22980, AT1G23040, AT1G23050, AT1G23060, AT1G23110, AT1G23150, AT1G23170, AT1G23230, AT1G23270, AT1G23510, AT1G23530, AT1G23540, AT1G23650, AT1G23830, AT1G23840, AT1G23850, AT1G24050, AT1G24060, AT1G24145, AT1G24160, AT1G24270, AT1G24310, AT1G24370, AT1G24380, AT1G24390, AT1G24460, AT1G24560, AT1G24575, AT1G24600, AT1G24706, AT1G24822, AT1G24851, AT1G24938, AT1G24996, AT1G25025, AT1G25097, AT1G25112, AT1G25170, AT1G25180, AT1G25275, AT1G25400, AT1G25425, AT1G25540, AT1G26110, AT1G26140, AT1G26180, AT1G26210, AT1G26290, AT1G26350, AT1G26600, AT1G26650, AT1G26665, AT1G26710, AT1G26720, AT1G26750, AT1G27020, AT1G27030, AT1G27090, AT1G27300, AT1G27385, AT1G27435, AT1G27510, AT1G27550, AT1G27610, AT1G27640, AT1G27670, AT1G27690, AT1G27695, AT1G27710, AT1G27790, AT1G27850, AT1G27990, AT1G28060, AT1G28080, AT1G28100, AT1G28135, AT1G28140, AT1G28150, AT1G28190, AT1G28240, AT1G28250, AT1G28260, AT1G28327, AT1G28375, AT1G28395, AT1G28400, AT1G28530, AT1G28540, AT1G28560, AT1G28630, AT1G28760, AT1G29010, AT1G29170, AT1G29179, AT1G29195, AT1G29270, AT1G29290, AT1G29300, AT1G29355, AT1G29480, AT1G29530, AT1G29540, AT1G29560, AT1G29580, AT1G29610, AT1G29620, AT1G29820, AT1G29830, AT1G29970, AT1G29980, AT1G30050, AT1G30190, AT1G30250, AT1G30260, AT1G30475, AT1G30515, AT1G30757, AT1G30795, AT1G30814, AT1G30835, AT1G30845, AT1G30850, AT1G30880, AT1G31050, AT1G31060, AT1G31130, AT1G31150, AT1G31175, AT1G31200, AT1G31250, AT1G31270, AT1G31335, AT1G31460, AT1G31520, AT1G31580, AT1G31620, AT1G31750, AT1G31772, AT1G31835, AT1G31870, AT1G31940, AT1G31960, AT1G31990, AT1G32000, AT1G32010, AT1G32040, AT1G32260, AT1G32290, AT1G52155, AT1G52220, AT1G52270, AT1G52320,
AT1G32310, AT1G32337, AT1G32370, AT1G32390, AT1G52390, AT1G52410, AT1G52430, AT1G52440,
AT1G32460, AT1G32570, AT1G32583, AT1G32610, AT1G52450, AT1G52550, AT1G52565, AT1G52615,
AT1G32630, AT1G32650, AT1G32670, AT1G32680, AT1G52680, AT1G52720, AT1G52780, AT1G52825,
AT1G32690, AT1G32720, AT1G32810, AT1G32920, AT1G52827, AT1G52840, AT1G52855, AT1G52905,
AT1G32928, AT1G32975, AT1G33055, AT1G33135, AT1G53035, AT1G53040, AT1G53180, AT1G53250,
AT1G33490, AT1G33500, AT1G33607, AT1G33640, AT1G53260, AT1G53265, AT1G53285, AT1G53380,
AT1G33700, AT1G33710, AT1G33810, AT1G33820, AT1G53400, AT1G53450, AT1G53460, AT1G53480,
AT1G33850, AT1G33860, AT1G34000, AT1G34010, AT1G53490, AT1G53560, AT1G53610, AT1G53620,
AT1G34047, AT1G34095, AT1G34245, AT1G34280, AT1G53625, AT1G53640, AT1G53645, AT1G53760,
AT1G34315, AT1G34350, AT1G34400, AT1G34440, AT1G53770, AT1G53785, AT1G53800, AT1G53935,
AT1G34490, AT1G34520, AT1G34550, AT1G34570, AT1G53970, AT1G54110, AT1G54120, AT1G54180,
AT1G34590, AT1G34630, AT1G34640, AT1G34730, AT1G54200, AT1G54215, AT1G54217, AT1G54300,
AT1G34770, AT1G34910, AT1G35030, AT1G35040, AT1G54420, AT1G54445, AT1G54470, AT1G54575,
AT1G35080, AT1G35100, AT1G35183, AT1G35230, AT1G54640, AT1G54680, AT1G54700, AT1G54720,
AT1G35320, AT1G35340, AT1G35375, AT1G35430, AT1G54730, AT1G54740, AT1G54770, AT1G54780,
AT1G35435, AT1G35500, AT1G35513, AT1G35570, AT1G54840, AT1G54860, AT1G54880, AT1G54920,
AT1G35614, AT1G35617, AT1G35640, AT1G35663, AT1G54923, AT1G54926, AT1G54950, AT1G54955,
AT1G35780, AT1G35820, AT1G35880, AT1G35890, AT1G54970, AT1G55080, AT1G55160, AT1G55220,
AT1G35900, AT1G36020, AT1G36100, AT1G36230, AT1G55250, AT1G55330, AT1G55365, AT1G55400,
AT1G36320, AT1G36380, AT1G36395, AT1G36640, AT1G55475, AT1G55535, AT1G55540, AT1G55545,
AT1G36670, AT1G36675, AT1G36745, AT1G36756, AT1G55675, AT1G55710, AT1G55800, AT1G55928,
AT1G36763, AT1G36925, AT1G36940, AT1G36960, AT1G55990, AT1G56020, AT1G56060, AT1G56085,
AT1G36970, AT1G36990, AT1G37000, AT1G37010, AT1G56100, AT1G56180, AT1G56200, AT1G56260,
AT1G37015, AT1G37037, AT1G37045, AT1G38380, AT1G56270, AT1G56320, AT1G56415, AT1G56420,
AT1G38630, AT1G38790, AT1G38950, AT1G39350, AT1G56530, AT1G56553, AT1G56555, AT1G56660,
AT1G40080, AT1G40087, AT1G40115, AT1G40125, AT1G57540, AT1G57565, AT1G57670, AT1G57680,
AT1G40129, AT1G40133, AT1G40230, AT1G41650, AT1G57760, AT1G58055, AT1G58120, AT1G58150,
AT1G41750, AT1G41770, AT1G41810, AT1G41820, AT1G58225, AT1G58235, AT1G58242, AT1G58250,
AT1G41855, AT1G41870, AT1G41900, AT1G41920, AT1G58330, AT1G58420, AT1G58460, AT1G58520,
AT1G42080, AT1G42190, AT1G42367, AT1G42393, AT1G58766, AT1G59077, AT1G59510, AT1G59520,
AT1G42430, AT1G42515, AT1G42550, AT1G42580, AT1G59535, AT1G59590, AT1G59600, AT1G59722,
AT1G42630, AT1G42700, AT1G42710, AT1G42740, AT1G59835, AT1G59840, AT1G59865, AT1G59885,
AT1G42960, AT1G43205, AT1G43230, AT1G43310, AT1G59920, AT1G59930, AT1G60000, AT1G60010,
AT1G43320, AT1G43330, AT1G43415, AT1G43570, AT1G60060, AT1G60240, AT1G60250, AT1G60380,
AT1G43580, AT1G43590, AT1G43660, AT1G43720, AT1G60460, AT1G60560, AT1G60610, AT1G60640,
AT1G43730, AT1G43777, AT1G43790, AT1G43810, AT1G60720, AT1G60870, AT1G60983, AT1G60987,
AT1G43850, AT1G43920, AT1G43940, AT1G43970, AT1G61000, AT1G61030, AT1G61080, AT1G61090,
AT1G44000, AT1G44010, AT1G44085, AT1G44222, AT1G61095, AT1G61097, AT1G61100, AT1G61170,
AT1G44414, AT1G44740, AT1G44770, AT1G44780, AT1G61200, AT1G61255, AT1G61340, AT1G61410,
AT1G44850, AT1G44875, AT1G44920, AT1G44930, AT1G61450, AT1G61688, AT1G61780, AT1G61900,
AT1G44960, AT1G44990, AT1G45150, AT1G45165, AT1G61920, AT1G62000, AT1G62045, AT1G62060,
AT1G45170, AT1G45230, AT1G45233, AT1G45248, AT1G62070, AT1G62080, AT1G62190, AT1G62210,
AT1G45403, AT1G45688, AT1G46336, AT1G47200, AT1G62220, AT1G62225, AT1G62240, AT1G62250,
AT1G47280, AT1G47310, AT1G47317, AT1G47395, AT1G62440, AT1G62480, AT1G62690, AT1G62780,
AT1G47400, AT1G47410, AT1G47420, AT1G47485, AT1G62855, AT1G62870, AT1G62890, AT1G62935,
AT1G47495, AT1G47640, AT1G47660, AT1G47680, AT1G63055, AT1G63060, AT1G63105, AT1G63240,
AT1G47690, AT1G47700, AT1G47770, AT1G47783, AT1G63245, AT1G63300, AT1G63310, AT1G63522,
AT1G47813, AT1G47820, AT1G47940, AT1G47970, AT1G63530, AT1G63535, AT1G63540, AT1G63610,
AT1G48145, AT1G48170, AT1G48200, AT1G48250, AT1G63670, AT1G63720, AT1G63960, AT1G64050,
AT1G48280, AT1G48290, AT1G48325, AT1G48330, AT1G64080, AT1G64107, AT1G64140, AT1G64180,
AT1G48360, AT1G48380, AT1G48440, AT1G48460, AT1G64295, AT1G64320, AT1G64330, AT1G64340,
AT1G48510, AT1G48530, AT1G48580, AT1G48720, AT1G64355, AT1G64360, AT1G64370, AT1G64385,
AT1G48730, AT1G48780, AT1G48840, AT1G49000, AT1G64405, AT1G64490, AT1G64560, AT1G64680,
AT1G49005, AT1G49110, AT1G49140, AT1G49150, AT1G64690, AT1G64700, AT1G64800, AT1G64870,
AT1G49260, AT1G49290, AT1G49310, AT1G49330, AT1G64990, AT1G65010, AT1G65090, AT1G65110,
AT1G49410, AT1G49490, AT1G49500, AT1G49510, AT1G65120, AT1G65130, AT1G65200, AT1G65230,
AT1G49680, AT1G49700, AT1G49715, AT1G49800, AT1G65270, AT1G65295, AT1G65342, AT1G65352,
AT1G49840, AT1G49870, AT1G49930, AT1G49940, AT1G65470, AT1G65490, AT1G65500, AT1G65510,
AT1G49975, AT1G50020, AT1G50080, AT1G50150, AT1G65710, AT1G65720, AT1G65845, AT1G66070,
AT1G50220, AT1G50290, AT1G50350, AT1G50530, AT1G66080, AT1G66145, AT1G66190, AT1G66235,
AT1G50660, AT1G50710, AT1G50730, AT1G50800, AT1G66245, AT1G66480, AT1G66790, AT1G66820,
AT1G50910, AT1G50930, AT1G51000, AT1G51010, AT1G66840, AT1G66890, AT1G66940, AT1G67025,
AT1G51030, AT1G51080, AT1G51100, AT1G51130, AT1G67035, AT1G67040, AT1G67050, AT1G67060,
AT1G51355, AT1G51400, AT1G51405, AT1G51430, AT1G67080, AT1G67170, AT1G67195, AT1G67230,
AT1G51840, AT1G51915, AT1G51920, AT1G51970, AT1G67350, AT1G67540, AT1G67635, AT1G67670,
AT1G52080, AT1G52087, AT1G52090, AT1G52140, AT1G67700, AT1G67775, AT1G67790, AT1G67855, AT1G67860, AT1G67865, AT1G67870, AT1G67910, AT2G03810, AT2G03830, AT2G03932, AT2G03937,
AT1G67920, AT1G67930, AT1G67950, AT1G68250, AT2G04000, AT2G04025, AT2G04034, AT2G04039,
AT1G68330, AT1G68350, AT1G68430, AT1G68440, AT2G04045, AT2G04046, AT2G04063, AT2G04135,
AT1G68490, AT1G68500, AT1G68680, AT1G68700, AT2G04235, AT2G04280, AT2G04305, AT2G04320,
AT1G68725, AT1G68765, AT1G68790, AT1G68795, AT2G04340, AT2G04360, AT2G04370, AT2G04380,
AT1G68845, AT1G68870, AT1G68875, AT1G68905, AT2G04410, AT2G04460, AT2G04480, AT2G04495,
AT1G68907, AT1G68910, AT1G68935, AT1G68945, AT2G04515, AT2G04600, AT2G04675, AT2G04790,
AT1G69050, AT1G69160, AT1G69170, AT1G69230, AT2G04795, AT2G04800, AT2G04870, AT2G04925,
AT1G69280, AT1G69320, AT1G69380, AT1G69390, AT2G05000, AT2G05030, AT2G05117, AT2G05120,
AT1G69430, AT1G69470, AT1G69760, AT1G69825, AT2G05185, AT2G05270, AT2G05290, AT2G05310,
AT1G69935, AT1G69970, AT1G69980, AT1G70100, AT2G05350, AT2G05360, AT2G05370, AT2G05500,
AT1G70160, AT1G70200, AT1G70220, AT1G70350, AT2G05564, AT2G05620, AT2G05645, AT2G05647,
AT1G70470, AT1G70505, AT1G70620, AT1G70760, AT2G05752, AT2G05915, AT2G05950, AT2G06005,
AT1G70770, AT1G70780, AT1G70895, AT1G70900, AT2G06010, AT2G06040, AT2G06095, AT2G06140,
AT1G70985, AT1G70990, AT1G71015, AT1G71080, AT2G06166, AT2G06200, AT2G06230, AT2G06390,
AT1G71110, AT1G71190, AT1G71235, AT1G71240, AT2G06420, AT2G06480, AT2G06555, AT2G06570,
AT1G71310, AT1G71430, AT1G71470, AT1G71730, AT2G06620, AT2G06630, AT2G06645, AT2G06750,
AT1G71740, AT1G71760, AT1G71780, AT1G71865, AT2G06775, AT2G06820, AT2G06906, AT2G06908,
AT1G71910, AT1G71940, AT1G72020, AT1G72080, AT2G06914, AT2G07000, AT2G07190, AT2G07215,
AT1G72240, AT1G72380, AT1G72390, AT1G72410, AT2G07280, AT2G07290, AT2G07310, AT2G07440,
AT1G72420, AT1G72430, AT1G72490, AT1G72530, AT2G07505, AT2G07520, AT2G07669, AT2G07672,
AT1G72580, AT1G72600, AT1G72645, AT1G72690, AT2G07673, AT2G07674, AT2G07676, AT2G07678,
AT1G72720, AT1G72790, AT1G73060, AT1G73090, AT2G07679, AT2G07691, AT2G07692, AT2G07701,
AT1G73120, AT1G73130, AT1G73165, AT1G73177, AT2G07702, AT2G07705, AT2G07706, AT2G07708,
AT1G73240, AT1G73350, AT1G73470, AT1G73510, AT2G07710, AT2G07713, AT2G07714, AT2G07719,
AT1G73603, AT1G73607, AT1G73770, AT1G73790, AT2G07721, AT2G07722, AT2G07724, AT2G07728,
AT1G73840, AT1G73885, AT1G73940, AT1G73965, AT2G07738, AT2G07760, AT2G07772, AT2G07773,
AT1G73970, AT1G74045, AT1G74055, AT1G74160, AT2G07774, AT2G07775, AT2G07776, AT2G07777,
AT1G74220, AT1G74530, AT1G74860, AT1G74880, AT2G07779, AT2G07787, AT2G07795, AT2G07880,
AT1G75060, AT1G75110, AT1G75150, AT1G75160, AT2G07981, AT2G08986, AT2G09388, AT2G09840,
AT1G75180, AT1G75190, AT1G75260, AT1G75310, AT2G09865, AT2G09900, AT2G10020, AT2G10070,
AT1G75360, AT1G75550, AT1G75730, AT1G75770, AT2G10090, AT2G10105, AT2G10110, AT2G10175,
AT1G75810, AT1G75860, AT1G75870, AT1G76070, AT2G10285, AT2G10340, AT2G10360, AT2G10380,
AT1G76185, AT1G76200, AT1G76230, AT1G76250, AT2G10390, AT2G10470, AT2G10550, AT2G10555,
AT1G76340, AT1G76405, AT1G76450, AT1G76480, AT2G10560, AT2G10602, AT2G10608, AT2G10850,
AT1G76600, AT1G76610, AT1G76660, AT1G76740, AT2G10870, AT2G10920, AT2G10930, AT2G10965,
AT1G76780, AT1G76820, AT1G76840, AT1G76850, AT2G10975, AT2G10980, AT2G11005, AT2G11015,
AT1G76910, AT1G76955, AT1G76960, AT1G76965, AT2G11090, AT2G11135, AT2G11370, AT2G11405,
AT1G76980, AT1G77150, AT1G77270, AT1G77310, AT2G11462, AT2G11570, AT2G11620, AT2G11626,
AT1G77350, AT1G77400, AT1G77500, AT1G77540, AT2G11775, AT2G11910, AT2G12110, AT2G12120,
AT1G77655, AT1G77765, AT1G77855, AT1G77885, AT2G12130, AT2G12170, AT2G12290, AT2G12320,
AT1G77890, AT1G77910, AT1G77960, AT1G78030, AT2G12400, AT2G12405, AT2G12465, AT2G12475,
AT1G78070, AT1G78110, AT1G78150, AT1G78170, AT2G12505, AT2G12610, AT2G12685, AT2G12700,
AT1G78650, AT1G78790, AT1G78810, AT1G78815, AT2G12875, AT2G12905, AT2G12935, AT2G12945,
AT1G78880, AT1G78890, AT1G78895, AT1G78995, AT2G13125, AT2G13126, AT2G13270, AT2G13320,
AT1G79020, AT1G79060, AT1G79070, AT1G79090, AT2G13430, AT2G13450, AT2G13500, AT2G13510,
AT1G79100, AT1G79110, AT1G79160, AT1G79170, AT2G13550, AT2G13650, AT2G13660, AT2G13690,
AT1G79200, AT1G79260, AT1G79390, AT1G79420, AT2G13730, AT2G13760, AT2G13770, AT2G13865,
AT1G79430, AT1G79660, AT1G79830, AT1G79915, AT2G13975, AT2G14000, AT2G14020, AT2G14045,
AT1G79970, AT1G79975, AT1G80000, AT1G80110, AT2G14095, AT2G14240, AT2G14247, AT2G14340,
AT1G80180, AT1G80200, AT1G80210, AT1G80240, AT2G14390, AT2G14460, AT2G14590, AT2G14600,
AT1G80245, AT1G80310, AT1G80540, AT1G80610, AT2G14635, AT2G14680, AT2G14700, AT2G14730,
AT1G80700, AT1G80810, AT1G80860, AT1G80865, AT2G14760, AT2G14774, AT2G14800, AT2G14810,
AT1G80890, AT1G80910, AT1G80940, AT1G80980, AT2G14850, AT2G14890, AT2G14910, AT2G14935,
AT2G01031, AT2G01060, AT2G01100, AT2G01120, AT2G15000, AT2G15020, AT2G15185, AT2G15290,
AT2G01175, AT2G01200, AT2G01300, AT2G01310, AT2G15327, AT2G15340, AT2G15345, AT2G15420,
AT2G01340, AT2G01400, AT2G01505, AT2G01580, AT2G15500, AT2G15520, AT2G15535, AT2G15550,
AT2G01590, AT2G01620, AT2G01640, AT2G01650, AT2G15600, AT2G15670, AT2G15800, AT2G15815,
AT2G01670, AT2G01755, AT2G01800, AT2G01870, AT2G15830, AT2G15860, AT2G15880, AT2G15890,
AT2G01913, AT2G01940, AT2G01960, AT2G01990, AT2G15930, AT2G15960, AT2G16015, AT2G16020,
AT2G02070, AT2G02280, AT2G02350, AT2G02370, AT2G16070, AT2G16170, AT2G16190, AT2G16200,
AT2G02440, AT2G02490, AT2G02510, AT2G02515, AT2G16270, AT2G16340, AT2G16365, AT2G16385,
AT2G02520, AT2G02795, AT2G02835, AT2G02840, AT2G16410, AT2G16485, AT2G16575, AT2G16586,
AT2G02880, AT2G02910, AT2G02950, AT2G03010, AT2G16595, AT2G16610, AT2G16630, AT2G16676, AT2G16820,
AT2G03070, AT2G03150, AT2G03180, AT2G03310, AT2G17110, AT2G17160, AT2G17240, AT2G17300,
AT2G03320, AT2G03420, AT2G03440, AT2G03540, AT2G17320, AT2G17340, AT2G17350, AT2G17442,
AT2G03570, AT2G03580, AT2G03630, AT2G03680, AT2G17540, AT2G17550, AT2G17695, AT2G17710, AT2G17723, AT2G17780, AT2G17785, AT2G17787, AT2G17960, AT2G17972, AT2G17990, AT2G18070, AT2G18200, AT2G18210, AT2G18240, AT2G18270, AT2G18410, AT2G18440, AT2G18610, AT2G18680, AT2G18690, AT2G18830, AT2G18870, AT2G18876, AT2G18910, AT2G18920, AT2G18930, AT2G18970, AT2G19000, AT2G19090, AT2G19180, AT2G19200, AT2G19220, AT2G19270, AT2G19290, AT2G19300, AT2G19320, AT2G19340, AT2G19390, AT2G19420, AT2G19460, AT2G19530, AT2G19700, AT2G19802, AT2G19850, AT2G19893, AT2G19950, AT2G20080, AT2G20142, AT2G20150, AT2G20208, AT2G20230, AT2G20240, AT2G20250, AT2G20310, AT2G20390, AT2G20410, AT2G20463, AT2G20480, AT2G20495, AT2G20500, AT2G20515, AT2G20585, AT2G20590, AT2G20595, AT2G20616, AT2G20620, AT2G20625, AT2G20700, AT2G20740, AT2G20760, AT2G20820, AT2G20825, AT2G20835, AT2G20870, AT2G20875, AT2G20890, AT2G20920, AT2G20970, AT2G20980, AT2G21080, AT2G21180, AT2G21185, AT2G21195, AT2G21237, AT2G21290, AT2G21385, AT2G21465, AT2G21560, AT2G21640, AT2G21660, AT2G21720, AT2G21725, AT2G21780, AT2G21800, AT2G21820, AT2G21870, AT2G21960, AT2G21970, AT2G21980, AT2G22000, AT2G22080, AT2G22121, AT2G22122, AT2G22140, AT2G22270, AT2G22320, AT2G22340, AT2G22470, AT2G22510, AT2G22520, AT2G22560, AT2G22790, AT2G22795, AT2G22805, AT2G22807, AT2G22820, AT2G22840, AT2G22890, AT2G22905, AT2G22940, AT2G22941, AT2G23040, AT2G23090, AT2G23093, AT2G23110, AT2G23120, AT2G23130, AT2G23270, AT2G23370, AT2G23390, AT2G23440, AT2G23490, AT2G23530, AT2G23670, AT2G23690, AT2G23755, AT2G23920, AT2G23985, AT2G24100, AT2G24285, AT2G24310, AT2G24330, AT2G24340, AT2G24410, AT2G24440, AT2G24460, AT2G24550, AT2G24617, AT2G24625, AT2G24762, AT2G24780, AT2G24910, AT2G24945, AT2G24960, AT2G24970, AT2G25185, AT2G25250, AT2G25260, AT2G25270, AT2G25510, AT2G25565, AT2G25605, AT2G25625, AT2G25670, AT2G25680, AT2G25685, AT2G25720, AT2G25735, AT2G25920, AT2G25930, AT2G25990, AT2G26110, AT2G26120, AT2G26340, AT2G26520, AT2G26770, AT2G26810, AT2G26840, AT2G26880, AT2G27090, AT2G27100, AT2G27180, AT2G27250, AT2G27280, AT2G27285, AT2G27315, AT2G27380, AT2G27385, AT2G27390, AT2G27402, AT2G27535, AT2G27540, AT2G27630, AT2G27650, AT2G27730, AT2G27775, AT2G27830, AT2G27840, AT2G27950, AT2G28020, AT2G28130, AT2G28230, AT2G28240, AT2G28330, AT2G28410, AT2G28430, AT2G28540, AT2G28570, AT2G28605, AT2G28625, AT2G28725, AT2G28755, AT2G28780, AT2G28870, AT2G28910, AT2G29045, AT2G29180, AT2G29620, AT2G29790, AT2G29880, AT2G29920, AT2G29995, AT2G30115, AT2G30120, AT2G30230, AT2G30280, AT2G30350, AT2G30370, AT2G30380, AT2G30395, AT2G30430, AT2G30480, AT2G30505, AT2G30560, AT2G30680, AT2G30700, AT2G30760, AT2G30820, AT2G30925, AT2G30930, AT2G30942, AT2G30960, AT2G30985, AT2G31035, AT2G31040, AT2G31081, AT2G31082, AT2G31083, AT2G31085, AT2G31090, AT2G31120, AT2G31130, AT2G31150, AT2G31160, AT2G31270, AT2G31345, AT2G31410, AT2G31480, AT2G31490, AT2G31590, AT2G31600, AT2G31700, AT2G31710, AT2G31751, AT2G31850, AT2G31930, AT2G31945, AT2G32130, AT2G32190, AT2G32200, AT2G32210, AT2G32235, AT2G32240, AT2G32275, AT2G32380, AT2G32760, AT2G32840, AT2G32890, AT2G32970, AT2G32980, AT2G33180, AT2G33233, AT2G33250, AT2G33390, AT2G33400, AT2G33435, AT2G33470, AT2G33490, AT2G33520, AT2G33585, AT2G33690, AT2G33720, AT2G33793, AT2G33850, AT2G33855, AT2G34010, AT2G34100, AT2G34110, AT2G34120, AT2G34123, AT2G34150, AT2G34185, AT2G34220, AT2G34230, AT2G34240, AT2G34270, AT2G34310, AT2G34315, AT2G34330, AT2G34510, AT2G34530, AT2G34580, AT2G34585, AT2G34640, AT2G34655, AT2G34670, AT2G34690, AT2G34730, AT2G34780, AT2G34800, AT2G34870, AT2G34910, AT2G35070, AT2G35075, AT2G35080, AT2G35090, AT2G35110, AT2G35200, AT2G35215, AT2G35230, AT2G35260, AT2G35290, AT2G35470, AT2G35480, AT2G35585, AT2G35612, AT2G35670, AT2G35710, AT2G35733, AT2G35736, AT2G35750, AT2G35790, AT2G35810, AT2G35820, AT2G35830, AT2G35850, AT2G35870, AT2G35900, AT2G35950, AT2G36030, AT2G36040, AT2G36145, AT2G36220, AT2G36255, AT2G36295, AT2G36400, AT2G36420, AT2G36440, AT2G36485, AT2G36550, AT2G36695, AT2G36724, AT2G36835, AT2G36885, AT2G36895, AT2G36920, AT2G36940, AT2G37035, AT2G37070, AT2G37080, AT2G37100, AT2G37195, AT2G37300, AT2G37370, AT2G37380, AT2G37530, AT2G37610, AT2G37680, AT2G37750, AT2G37860, AT2G37910, AT2G37920, AT2G37975, AT2G38090, AT2G38140, AT2G38160, AT2G38220, AT2G38350, AT2G38430, AT2G38440, AT2G38465, AT2G38570, AT2G38580, AT2G38690, AT2G38695, AT2G38790, AT2G38823, AT2G38890, AT2G39000, AT2G39160, AT2G39170, AT2G39200, AT2G39300, AT2G39370, AT2G39500, AT2G39520, AT2G39560, AT2G39680, AT2G39855, AT2G39870, AT2G39950, AT2G40020, AT2G40060, AT2G40070, AT2G40085, AT2G40095, AT2G40113, AT2G40316, AT2G40390, AT2G40410, AT2G40475, AT2G40530, AT2G40550, AT2G40630, AT2G40680, AT2G40765, AT2G40955, AT2G41150, AT2G41230, AT2G41260, AT2G41280, AT2G41350, AT2G41390, AT2G41400, AT2G41420, AT2G41440, AT2G41570, AT2G41610, AT2G41650, AT2G41730, AT2G41760, AT2G41770, AT2G41780, AT2G41800, AT2G41810, AT2G41905, AT2G41945, AT2G41960, AT2G41990, AT2G42040, AT2G42050, AT2G42130, AT2G42180, AT2G42190, AT2G42260, AT2G42280, AT2G42310, AT2G42320, AT2G42340, AT2G42370, AT2G42395, AT2G42540, AT2G42610, AT2G42640, AT2G42760, AT2G42840, AT2G42860, AT2G42900, AT2G42950, AT2G42955, AT2G42975, AT2G43110, AT2G43250, AT2G43390, AT2G43450, AT2G43540, AT2G43630, AT2G43780, AT2G43795, AT2G43945, AT2G43950, AT2G43990, AT2G44010, AT2G44080, AT2G44195, AT2G44200, AT2G44280, AT2G44420, AT2G44510, AT2G44600, AT2G44640, AT2G44735, AT2G44740, AT2G44760, AT2G44820, AT2G44850, AT2G45000, AT2G45060, AT2G45250, AT2G45260, AT2G45380, AT2G45403, AT2G45450, AT2G45480, AT2G45520, AT2G45690, AT2G45780, AT2G45860, AT2G45900, AT2G45930, AT2G45980, AT2G46000, AT2G46060, AT2G46080, AT2G46180, AT2G46200, AT2G46250, AT2G46360, AT2G46375, AT2G46380, AT2G46390, AT2G46455, AT2G46490, AT2G46540, AT2G46550, AT2G46640, AT2G46735, AT2G46820, AT2G46830, AT2G46915, AT2G46940, AT2G46980, AT2G47010, AT2G47020, AT2G47115, AT2G47200, AT2G47360, AT2G47480, AT2G47485, AT2G47530, AT2G47660, AT2G47690, AT2G47720, AT3G15230, AT3G15240, AT3G15250, AT3G15280,
AT2G47840, AT2G47910, AT2G47930, AT2G47950, AT3G15310, AT3G15340, AT3G15351, AT3G15357,
AT2G48040, AT2G48050, AT2G48060, AT2G48070, AT3G15358, AT3G15395, AT3G15400, AT3G15420,
AT2G48075, AT2G48090, AT2G48120, AT3G01060, AT3G15440, AT3G15550, AT3G15560, AT3G15630,
AT3G01130, AT3G01160, AT3G01170, AT3G01230, AT3G15750, AT3G15760, AT3G15770, AT3G15780,
AT3G01240, AT3G01250, AT3G01323, AT3G01325, AT3G15820, AT3G15830, AT3G15840, AT3G15860,
AT3G01345, AT3G01430, AT3G01435, AT3G01513, AT3G15900, AT3G15910, AT3G15950, AT3G16000,
AT3G01516, AT3G01670, AT3G01680, AT3G01700, AT3G16040, AT3G16070, AT3G16200, AT3G16220,
AT3G01710, AT3G01720, AT3G01730, AT3G01740, AT3G16330, AT3G16660, AT3G16670, AT3G16750,
AT3G01810, AT3G01860, AT3G01940, AT3G01950, AT3G16895, AT3G16930, AT3G17120, AT3G17155,
AT3G01960, AT3G02120, AT3G02125, AT3G02170, AT3G17160, AT3G17190, AT3G17350, AT3G17460,
AT3G02180, AT3G02220, AT3G02240, AT3G02370, AT3G17580, AT3G17780, AT3G17890, AT3G17900,
AT3G02390, AT3G02420, AT3G02500, AT3G02555, AT3G17930, AT3G17950, AT3G18050, AT3G18240,
AT3G02560, AT3G02640, AT3G02670, AT3G02680, AT3G18250, AT3G18300, AT3G18310, AT3G18350,
AT3G02790, AT3G02860, AT3G02900, AT3G02930, AT3G18410, AT3G18485, AT3G18510, AT3G18540,
AT3G03020, AT3G03070, AT3G03130, AT3G03150, AT3G18560, AT3G18700, AT3G18770, AT3G18800,
AT3G03160, AT3G03170, AT3G03210, AT3G03420, AT3G18940, AT3G19020, AT3G19030, AT3G19055,
AT3G03460, AT3G03560, AT3G03570, AT3G03770, AT3G19120, AT3G19180, AT3G19200, AT3G19220,
AT3G03773, AT3G03870, AT3G03930, AT3G04020, AT3G19250, AT3G19330, AT3G19340, AT3G19530,
AT3G04040, AT3G04160, AT3G04310, AT3G04510, AT3G19540, AT3G19550, AT3G19650, AT3G19660,
AT3G04550, AT3G04560, AT3G04640, AT3G04740, AT3G19750, AT3G19790, AT3G19800, AT3G19900,
AT3G04903, AT3G04943, AT3G04945, AT3G04960, AT3G19920, AT3G20070, AT3G20155, AT3G20340,
AT3G04990, AT3G05010, AT3G05020, AT3G05080, AT3G20350, AT3G20362, AT3G20430, AT3G20450,
AT3G05110, AT3G05130, AT3G05220, AT3G05320, AT3G20490, AT3G20555, AT3G20557, AT3G20680,
AT3G05330, AT3G05410, AT3G05460, AT3G05550, AT3G20720, AT3G20760, AT3G20850, AT3G20865,
AT3G05570, AT3G05725, AT3G05727, AT3G05730, AT3G20900, AT3G20920, AT3G20980, AT3G21000,
AT3G05830, AT3G05900, AT3G05935, AT3G05937, AT3G21055, AT3G21080, AT3G21260, AT3G21290,
AT3G05980, AT3G06020, AT3G06070, AT3G06090, AT3G21320, AT3G21400, AT3G21465, AT3G21570,
AT3G06145, AT3G06180, AT3G06360, AT3G06435, AT3G21680, AT3G21710, AT3G21865, AT3G22070,
AT3G06545, AT3G06547, AT3G06600, AT3G06610, AT3G22090, AT3G22210, AT3G22231, AT3G22235,
AT3G06670, AT3G06710, AT3G06750, AT3G06780, AT3G22240, AT3G22270, AT3G22380, AT3G22415,
AT3G06790, AT3G06840, AT3G06870, AT3G06890, AT3G22430, AT3G22510, AT3G22680, AT3G22790,
AT3G06895, AT3G06960, AT3G07005, AT3G07150, AT3G22820, AT3G22840, AT3G22942, AT3G23040,
AT3G07180, AT3G07195, AT3G07210, AT3G07425, AT3G23165, AT3G23167, AT3G23170, AT3G23172,
AT3G07440, AT3G07510, AT3G07560, AT3G07568, AT3G23245, AT3G23290, AT3G23295, AT3G23440,
AT3G07580, AT3G07640, AT3G07710, AT3G07730, AT3G23590, AT3G23650, AT3G23715, AT3G23720,
AT3G07790, AT3G07910, AT3G07950, AT3G08030, AT3G23727, AT3G23740, AT3G23850, AT3G23860,
AT3G08490, AT3G08550, AT3G08610, AT3G08630, AT3G23910, AT3G24160, AT3G24180, AT3G24225,
AT3G08640, AT3G08650, AT3G08670, AT3G08780, AT3G24250, AT3G24255, AT3G24280, AT3G24380,
AT3G08880, AT3G08955, AT3G09000, AT3G09032, AT3G24490, AT3G24506, AT3G24508, AT3G24510,
AT3G09050, AT3G09085, AT3G09130, AT3G09162, AT3G24513, AT3G24517, AT3G24535, AT3G24630,
AT3G09180, AT3G09280, AT3G09430, AT3G09450, AT3G24640, AT3G24680, AT3G24690, AT3G24750,
AT3G09730, AT3G09750, AT3G09770, AT3G09860, AT3G24770, AT3G24780, AT3G25080, AT3G25130,
AT3G09922, AT3G09950, AT3G10020, AT3G10116, AT3G25200, AT3G25400, AT3G25545, AT3G25590,
AT3G10120, AT3G10195, AT3G10525, AT3G10572, AT3G25597, AT3G25640, AT3G25655, AT3G25690,
AT3G10650, AT3G10810, AT3G10830, AT3G10880, AT3G25720, AT3G25727, AT3G25805, AT3G25870,
AT3G10930, AT3G10980, AT3G11030, AT3G11060, AT3G25882, AT3G25905, AT3G26000, AT3G26110,
AT3G11160, AT3G11300, AT3G11310, AT3G11325, AT3G26235, AT3G26616, AT3G26710, AT3G26750,
AT3G11405, AT3G11560, AT3G11590, AT3G11600, AT3G26800, AT3G26850, AT3G26855, AT3G26890,
AT3G11640, AT3G11670, AT3G11690, AT3G11745, AT3G26910, AT3G26950, AT3G26960, AT3G27025,
AT3G11760, AT3G11800, AT3G11810, AT3G11860, AT3G27030, AT3G27050, AT3G27100, AT3G27130,
AT3G11880, AT3G12190, AT3G12210, AT3G12320, AT3G27210, AT3G27250, AT3G27350, AT3G27370,
AT3G12345, AT3G12510, AT3G12650, AT3G12840, AT3G27390, AT3G27420, AT3G27520, AT3G27590,
AT3G12870, AT3G12910, AT3G12920, AT3G12955, AT3G27630, AT3G27750, AT3G27770, AT3G27800,
AT3G12960, AT3G12970, AT3G12977, AT3G13130, AT3G27906, AT3G27930, AT3G27990, AT3G28020,
AT3G13175, AT3G13227, AT3G13240, AT3G13275, AT3G28110, AT3G28120, AT3G28155, AT3G28170,
AT3G13360, AT3G13370, AT3G13403, AT3G13410, AT3G28190, AT3G28240, AT3G28260, AT3G28280,
AT3G13420, AT3G13435, AT3G13460, AT3G13480, AT3G28350, AT3G28370, AT3G28420, AT3G28455,
AT3G13500, AT3G13520, AT3G13630, AT3G13674, AT3G28530, AT3G28560, AT3G28590, AT3G28670,
AT3G13677, AT3G13780, AT3G13845, AT3G13857, AT3G28720, AT3G28770, AT3G29010, AT3G29033,
AT3G13910, AT3G13950, AT3G13960, AT3G13980, AT3G29034, AT3G29075, AT3G29080, AT3G29130,
AT3G14060, AT3G14190, AT3G14280, AT3G14340, AT3G29140, AT3G29185, AT3G29210, AT3G29220,
AT3G14395, AT3G14430, AT3G14480, AT3G14560, AT3G29265, AT3G29280, AT3G29300, AT3G29305,
AT3G14595, AT3G14670, AT3G14750, AT3G14760, AT3G29385, AT3G29420, AT3G29450, AT3G29470,
AT3G14780, AT3G14830, AT3G14840, AT3G14870, AT3G29560, AT3G29570, AT3G29600, AT3G29610,
AT3G14880, AT3G14900, AT3G14910, AT3G14920, AT3G29636, AT3G29700, AT3G29763, AT3G29785,
AT3G15000, AT3G15095, AT3G15110, AT3G15115, AT3G29786, AT3G29790, AT3G29796, AT3G30150, AT3G30160, AT3G30190, AT3G30200, AT3G30220,
AT3G30250, AT3G30320, AT3G30350, AT3G30360,
AT3G30370, AT3G30490, AT3G30510, AT3G30520,
AT3G30580, AT3G30590, AT3G30610, AT3G30645,
AT3G30650, AT3G30660, AT3G30670, AT3G30690,
AT3G30700, AT3G30720, AT3G30725, AT3G30730,
AT3G30750, AT3G30751, AT3G30755, AT3G30816,
AT3G30820, AT3G30840, AT3G30843, AT3G30845,
AT3G30848, AT3G31300, AT3G31310, AT3G31320,
AT3G31330, AT3G31350, AT3G31370, AT3G31400,
AT3G31406, AT3G31430, AT3G31540, AT3G31900,
AT3G31910, AT3G31915, AT3G31940, AT3G31955,
AT3G32050, AT3G32070, AT3G32100, AT3G32120,
AT3G32150, AT3G32160, AT3G32180, AT3G32190,
AT3G32200, AT3G32330, AT3G32410, AT3G32896,
AT3G32902, AT3G32903, AT3G32904, AT3G32930,
AT3G32960, AT3G33064, AT3G33073, AT3G33080,
AT3G33131, AT3G33187, AT3G33230, AT3G33293,
AT3G33393, AT3G33448, AT3G33494, AT3G33572,
AT3G42070, AT3G42090, AT3G42120, AT3G42130,
AT3G42140, AT3G42190, AT3G42200, AT3G42240,
AT3G42250, AT3G42254, AT3G42300, AT3G42310,
AT3G42320, AT3G42350, AT3G42380, AT3G42390,
AT3G42430, AT3G42436, AT3G42473, AT3G42480,
AT3G42490, AT3G42510, AT3G42520, AT3G42540,
AT3G42556, AT3G42560, AT3G42590, AT3G42610,
AT3G42680, AT3G42700, AT3G42723, AT3G42725,
AT3G42740, AT3G42750, AT3G42780, AT3G42786,
AT3G42800, AT3G42810, AT3G42870, AT3G42920,
AT3G42970, AT3G42990, AT3G43110, AT3G43140,
AT3G43150, AT3G43153, AT3G43160, AT3G43260,
AT3G43280, AT3G43290, AT3G43330, AT3G43410,
AT3G43420, AT3G43450, AT3G43470, AT3G43480,
AT3G43500, AT3G43528, AT3G43580, AT3G43583,
AT3G43680, AT3G43682, AT3G43760, AT3G43770,
AT3G43833, AT3G43850, AT3G43863, AT3G43870,
AT3G43880, AT3G43900, AT3G43910, AT3G43930,
AT3G43940, AT3G43970, AT3G44020, AT3G44040,
AT3G44070, AT3G44115, AT3G44140, AT3G44150,
AT3G44170, AT3G44210, AT3G44230, AT3G44235,
AT3G44280, AT3G44370, AT3G44430, AT3G44440,
AT3G44450, AT3G44470, AT3G44570, AT3G44580,
AT3G44690, AT3G44716, AT3G44750, AT3G44755,
AT3G44760, AT3G44770, AT3G44935, AT3G44940,
AT3G44960, AT3G44980, AT3G45040, AT3G45050,
AT3G45093, AT3G45110, AT3G45120, AT3G45160,
AT3G45200, AT3G45230, AT3G45320, AT3G45360,
AT3G45370, AT3G45443, AT3G45577, AT3G45730,
AT3G45755, AT3G45820, AT3G45830, AT3G45900,
AT3G45910, AT3G46150, AT3G46220, AT3G46240,
AT3G46270, AT3G46300, AT3G46310, AT3G46360,
AT3G46380, AT3G46390, AT3G46430, AT3G46630,
AT3G46750, AT3G46880, AT3G46890, AT3G47070,
AT3G47100, AT3G47230, AT3G47240, AT3G47295,
AT3G47320, AT3G47410, AT3G47490, AT3G47510,
AT3G47630, AT3G47675, AT3G47833, AT3G47836,
AT3G47850, AT3G47920, AT3G47965, AT3G48020,
AT3G48120, AT3G48180, AT3G48185, AT3G48200,
AT3G48220, AT3G48231, AT3G48470, AT3G48490,
AT3G48510, AT3G48550, AT3G48630, AT3G48640,
AT3G48660, AT3G48675, AT3G48710, AT3G48860,
AT3G49055, AT3G49230, AT3G49250, AT3G49270,
AT3G49280, AT3G49290, AT3G49300, AT3G49305,
AT3G49307, AT3G49410, AT3G49460, AT3G49490,
AT3G49540, AT3G49550, AT3G49570, AT3G49580,
AT3G49590, AT3G49770, AT3G49790, AT3G49820,
AT3G49840, AT3G49890, AT3G49990, AT3G50040,
AT3G50250, AT3G50320, AT3G50340, AT3G50370,
AT3G50373, AT3G50376, AT3G50430, AT3G50540,
AT3G50550, AT3G50570, AT3G50580, AT3G50610,
AT3G50640, AT3G50685, AT3G50800, AT3G50900,
AT3G50910, AT3G50925, AT3G51010, AT3G51100,
AT3G51230, AT3G51290, AT3G51350, AT3G51500,
AT3G51510, AT3G51540, AT3G51580, AT3G51610,
AT3G51640, AT3G51650, AT3G51750, AT3G51890,
AT3G51970, AT3G52040, AT3G52070, AT3G52105,
AT3G52110, AT3G52115, AT3G52170, AT3G52220,
AT3G52230, AT3G52240, AT3G52360, AT3G52420,
AT3G52480, AT3G52520, AT3G52540, AT3G52550,
AT3G52620, AT3G52700, AT3G52710, AT3G52740,
AT3G52770, AT3G52860, AT3G53235, AT3G53270,
AT3G53320, AT3G53350, AT3G53470, AT3G53540,
AT3G53630, AT3G53670, AT3G53860, AT3G53970,
AT3G54000, AT3G54060, AT3G54170, AT3G54310,
AT3G54500, AT3G54520, AT3G54530, AT3G54630,
AT3G54680, AT3G54710, AT3G54730, AT3G54750,
AT3G54880, AT3G55060, AT3G55160, AT3G55250,
AT3G55420, AT3G55570, AT3G55600, AT3G55646,
AT3G55690, AT3G55720, AT3G55760, AT3G55790,
AT3G55860, AT3G55880, AT3G55910, AT3G55930,
AT3G56010, AT3G56160, AT3G56220, AT3G56250,
AT3G56260, AT3G56290, AT3G56360, AT3G56390,
AT3G56410, AT3G56430, AT3G56480, AT3G56500,
AT3G56590, AT3G56610, AT3G56650, AT3G56670,
AT3G56720, AT3G56750, AT3G56790, AT3G56870,
AT3G56910, AT3G57110, AT3G57160, AT3G57200,
AT3G57210, AT3G57320, AT3G57360, AT3G57400,
AT3G57420, AT3G57440, AT3G57450, AT3G57500,
AT3G57690, AT3G57780, AT3G57785, AT3G57850,
AT3G57860, AT3G57930, AT3G57950, AT3G57990,
AT3G58010, AT3G58020, AT3G58050, AT3G58080,
AT3G58110, AT3G58230, AT3G58280, AT3G58300,
AT3G58320, AT3G58330, AT3G58470, AT3G58480,
AT3G58540, AT3G58770, AT3G58840, AT3G58870,
AT3G59090, AT3G59300, AT3G59370, AT3G59390,
AT3G59430, AT3G59460, AT3G59490, AT3G59640,
AT3G59680, AT3G59800, AT3G59840, AT3G59870,
AT3G59880, AT3G59900, AT3G59930, AT3G60070,
AT3G60200, AT3G60230, AT3G60310, AT3G60320,
AT3G60380, AT3G60480, AT3G60520, AT3G60560,
AT3G60590, AT3G60650, AT3G60680, AT3G60760,
AT3G60850, AT3G60890, AT3G60930, AT3G61370,
AT3G61380, AT3G61500, AT3G61570, AT3G61660,
AT3G61670, AT3G61710, AT3G61780, AT3G61840,
AT3G61870, AT3G61898, AT3G61920, AT3G61930,
AT3G62070, AT3G62140, AT3G62320, AT3G62350,
AT3G62370, AT3G62380, AT3G62400, AT3G62450,
AT3G62480, AT3G62490, AT3G62500, AT3G62510,
AT3G62580, AT3G62640, AT3G62650, AT3G62680,
AT3G62730, AT3G62790, AT3G62920, AT3G62990,
AT3G63020, AT3G63040, AT3G63050, AT3G63100,
AT3G63160, AT3G63180, AT3G63270, AT3G63420,
AT3G63430, AT4G00280, AT4G00310, AT4G00355,
AT4G00440, AT4G00450, AT4G00525, AT4G00530,
AT4G00580, AT4G00585, AT4G00695, AT4G00770,
AT4G00890, AT4G00920, AT4G00930, AT4G00950,
AT4G00955, AT4G01090, AT4G01150, AT4G01170,
AT4G01245, AT4G01290, AT4G01340, AT4G01360,
AT4G01500, AT4G01525, AT4G01530, AT4G01535,
AT4G01590, AT4G01670, AT4G01735, AT4G01895,
AT4G01915, AT4G01935, AT4G01960, AT4G01985,
AT4G01995, AT4G02000, AT4G02030, AT4G02040,
AT4G02090, AT4G02140, AT4G02160, AT4G02170,
AT4G02210, AT4G02270, AT4G02425, AT4G02465, AT4G02482, AT4G02530, AT4G02550, AT4G02715,
AT4G02725, AT4G02760, AT4G02800, AT4G02810,
AT4G02830, AT4G02870, AT4G02880, AT4G02920,
AT4G03090, AT4G03150, AT4G03165, AT4G03180,
AT4G03305, AT4G03380, AT4G03505, AT4G03580,
AT4G03600, AT4G03620, AT4G03680, AT4G03740,
AT4G03750, AT4G03820, AT4G03940, AT4G03970,
AT4G03975, AT4G03979, AT4G04030, AT4G04155,
AT4G04190, AT4G04273, AT4G04330, AT4G04394,
AT4G04396, AT4G04398, AT4G04423, AT4G04470,
AT4G04480, AT4G04525, AT4G04614, AT4G04635,
AT4G04650, AT4G04730, AT4G04745, AT4G04820,
AT4G04925, AT4G04980, AT4G05070, AT4G05095,
AT4G05145, AT4G05290, AT4G05370, AT4G05400,
AT4G05523, AT4G05553, AT4G05560, AT4G05580,
AT4G05581, AT4G05616, AT4G05631, AT4G05632,
AT4G05636, AT4G05640, AT4G06490, AT4G06534,
AT4G06603, AT4G06637, AT4G06672, AT4G06676,
AT4G06716, AT4G06724, AT4G06728, AT4G06735,
AT4G06740, AT4G07380, AT4G07452, AT4G07460,
AT4G07485, AT4G07500, AT4G07515, AT4G07523,
AT4G07524, AT4G07526, AT4G07666, AT4G07675,
AT4G07740, AT4G07800, AT4G07825, AT4G07868,
AT4G07932, AT4G07940, AT4G07943, AT4G07965,
AT4G08013, AT4G08025, AT4G08028, AT4G08039,
AT4G08056, AT4G08097, AT4G08098, AT4G08111,
AT4G08130, AT4G08140, AT4G08200, AT4G08230,
AT4G08240, AT4G08270, AT4G08310, AT4G08330,
AT4G08336, AT4G08395, AT4G08485, AT4G08510,
AT4G08540, AT4G08555, AT4G08593, AT4G08602,
AT4G08630, AT4G08710, AT4G08730, AT4G08740,
AT4G08760, AT4G08810, AT4G08820, AT4G08868,
AT4G08869, AT4G08874, AT4G08875, AT4G08876,
AT4G08895, AT4G08910, AT4G09030, AT4G09060,
AT4G09070, AT4G09153, AT4G09170, AT4G09210,
AT4G09220, AT4G09260, AT4G09270, AT4G09290,
AT4G09390, AT4G09550, AT4G09580, AT4G09630,
AT4G09647, AT4G09680, AT4G09700, AT4G09840,
AT4G09850, AT4G09860, AT4G09880, AT4G09890,
AT4G09965, AT4G09970, AT4G09984, AT4G10060,
AT4G10080, AT4G10090, AT4G10140, AT4G10180,
AT4G10230, AT4G10265, AT4G10270, AT4G10330,
AT4G10613, AT4G10660, AT4G10670, AT4G10700,
AT4G10800, AT4G10810, AT4G10820, AT4G10845,
AT4G10860, AT4G10870, AT4G10890, AT4G10910,
AT4G10930, AT4G10970, AT4G11020, AT4G11100,
AT4G11211, AT4G11385, AT4G11393, AT4G11430,
AT4G11700, AT4G11720, AT4G11780, AT4G11870,
AT4G11910, AT4G11940, AT4G11990, AT4G12000,
AT4G12005, AT4G12070, AT4G12220, AT4G12350,
AT4G12370, AT4G12380, AT4G12540, AT4G12580,
AT4G12680, AT4G12700, AT4G12735, AT4G12760,
AT4G12770, AT4G12780, AT4G12930, AT4G12940,
AT4G12970, AT4G12990, AT4G13095, AT4G13140,
AT4G13150, AT4G13195, AT4G13200, AT4G13220,
AT4G13235, AT4G13266, AT4G13270, AT4G13320,
AT4G13340, AT4G13470, AT4G13500, AT4G13520,
AT4G13530, AT4G13540, AT4G13690, AT4G13740,
AT4G13955, AT4G13968, AT4G14100, AT4G14104,
AT4G14120, AT4G14200, AT4G14270, AT4G14272,
AT4G14276, AT4G14315, AT4G14380, AT4G14385,
AT4G14450, AT4G14530, AT4G14590, AT4G14615,
AT4G14650, AT4G14690, AT4G14723, AT4G14760,
AT4G14810, AT4G14950, AT4G14970, AT4G14990,
AT4G15030, AT4G15096, AT4G15140, AT4G15150,
AT4G15160, AT4G15460, AT4G15540, AT4G15563,
AT4G15640, AT4G15650, AT4G15710, AT4G15733,
AT4G15735, AT4G15820, AT4G15885, AT4G15950,
AT4G15970, AT4G15990, AT4G16000, AT4G16040,
AT4G16060, AT4G16090, AT4G16140, AT4G16170,
AT4G16215, AT4G16240, AT4G16320, AT4G16400,
AT4G16444, AT4G16447, AT4G16450, AT4G16460,
AT4G16515, AT4G16695, AT4G16810, AT4G16840,
AT4G16845, AT4G16850, AT4G16980, AT4G17000,
AT4G17010, AT4G17110, AT4G17130, AT4G17215,
AT4G17240, AT4G17250, AT4G17310, AT4G17430,
AT4G17540, AT4G17590, AT4G17600, AT4G17620,
AT4G17700, AT4G17713, AT4G17790, AT4G17930,
AT4G17960, AT4G17990, AT4G18000, AT4G18070,
AT4G18080, AT4G18090, AT4G18140, AT4G18280,
AT4G18310, AT4G18320, AT4G18335, AT4G18395,
AT4G18400, AT4G18420, AT4G18470, AT4G18490,
AT4G18500, AT4G18501, AT4G18510, AT4G18540,
AT4G18570, AT4G18580, AT4G18593, AT4G18600,
AT4G18610, AT4G18650, AT4G18660, AT4G18670,
AT4G18680, AT4G18690, AT4G18823, AT4G18830,
AT4G18850, AT4G18860, AT4G19070, AT4G19095,
AT4G19100, AT4G19140, AT4G19160, AT4G19190,
AT4G19200, AT4G19240, AT4G19270, AT4G19280,
AT4G19290, AT4G19305, AT4G19320, AT4G19350,
AT4G19360, AT4G19430, AT4G19480, AT4G19620,
AT4G19905, AT4G19950, AT4G19980, AT4G20020,
AT4G20095, AT4G20150, AT4G20160, AT4G20190,
AT4G20250, AT4G20290, AT4G20330, AT4G20350,
AT4G20390, AT4G20470, AT4G20500, AT4G20510,
AT4G20690, AT4G20715, AT4G20720, AT4G20880,
AT4G21010, AT4G21105, AT4G21140, AT4G21215,
AT4G21445, AT4G21460, AT4G21500, AT4G21620,
AT4G21700, AT4G21720, AT4G21740, AT4G21780,
AT4G21865, AT4G21890, AT4G21920, AT4G21950,
AT4G22000, AT4G22160, AT4G22190, AT4G22210,
AT4G22214, AT4G22217, AT4G22235, AT4G22270,
AT4G22320, AT4G22400, AT4G22420, AT4G22430,
AT4G22440, AT4G22470, AT4G22510, AT4G22600,
AT4G22740, AT4G22800, AT4G22830, AT4G22850,
AT4G22860, AT4G22920, AT4G22980, AT4G23020,
AT4G23090, AT4G23110, AT4G23330, AT4G23493,
AT4G23496, AT4G23610, AT4G23760, AT4G23770,
AT4G23780, AT4G23870, AT4G23880, AT4G23885,
AT4G23890, AT4G23910, AT4G23970, AT4G23990,
AT4G24030, AT4G24110, AT4G24150, AT4G24175,
AT4G24265, AT4G24275, AT4G24300, AT4G24370,
AT4G24410, AT4G24500, AT4G24590, AT4G24600,
AT4G24610, AT4G24680, AT4G24700, AT4G24720,
AT4G24900, AT4G24930, AT4G24950, AT4G24972,
AT4G24980, AT4G25030, AT4G25070, AT4G25170,
AT4G25315, AT4G25430, AT4G25510, AT4G25515,
AT4G25520, AT4G25620, AT4G25670, AT4G25690,
AT4G25760, AT4G25845, AT4G26020, AT4G26030,
AT4G26040, AT4G26060, AT4G26130, AT4G26170,
AT4G26190, AT4G26240, AT4G26290, AT4G26320,
AT4G26410, AT4G26450, AT4G26630, AT4G26850,
AT4G26960, AT4G26965, AT4G27020, AT4G27030,
AT4G27120, AT4G27330, AT4G27380, AT4G27390,
AT4G27410, AT4G27415, AT4G27430, AT4G27500,
AT4G27510, AT4G27530, AT4G27580, AT4G27595,
AT4G27610, AT4G27630, AT4G27652, AT4G27654,
AT4G27657, AT4G27660, AT4G27810, AT4G27850,
AT4G27930, AT4G27980, AT4G28005, AT4G28025,
AT4G28085, AT4G28100, AT4G28160, AT4G28170,
AT4G28180, AT4G28190, AT4G28210, AT4G28230,
AT4G28240, AT4G28260, AT4G28280, AT4G28290,
AT4G28310, AT4G28330, AT4G28340, AT4G28460,
AT4G28690, AT4G28740, AT4G28760, AT4G28770, AT4G28810, AT4G28840, AT4G28870, AT4G28920, AT4G28930, AT4G29020, AT4G29030, AT4G29200, AT4G29273, AT4G29280, AT4G29285, AT4G29290, AT4G29300, AT4G29305, AT4G29520, AT4G29560, AT4G29660, AT4G29780, AT4G29790, AT4G29870, AT4G29960, AT4G30010, AT4G30050, AT4G30064, AT4G30070, AT4G30074, AT4G30090, AT4G30130, AT4G30150, AT4G30230, AT4G30390, AT4G30450, AT4G30460, AT4G30630, AT4G30662, AT4G30670, AT4G30730, AT4G30740, AT4G30750, AT4G30770, AT4G30780, AT4G30790, AT4G30970, AT4G30993, AT4G31030, AT4G31080, AT4G31090, AT4G31115, AT4G31260, AT4G31280, AT4G31340, AT4G31380, AT4G31430, AT4G31440, AT4G31510, AT4G31550, AT4G31560, AT4G31570, AT4G31600, AT4G31730, AT4G31805, AT4G31830, AT4G31875, AT4G31880, AT4G31960, AT4G32020, AT4G32030, AT4G32080, AT4G32090, AT4G32100, AT4G32105, AT4G32110, AT4G32190, AT4G32230, AT4G32240, AT4G32460, AT4G32560, AT4G32590, AT4G32680, AT4G32695, AT4G32770, AT4G32860, AT4G32960, AT4G32970, AT4G33130, AT4G33310, AT4G33320, AT4G33380, AT4G33480, AT4G33560, AT4G33590, AT4G33600, AT4G33610, AT4G33625, AT4G33640, AT4G33660, AT4G33666, AT4G33690, AT4G33740, AT4G33750, AT4G33780, AT4G33800, AT4G33890, AT4G33925, AT4G33960, AT4G33970, AT4G33980, AT4G34080, AT4G34090, AT4G34190, AT4G34265, AT4G34412, AT4G34550, AT4G34560, AT4G34600, AT4G34630, AT4G34690, AT4G35170, AT4G35240, AT4G35295, AT4G35360, AT4G35400, AT4G35430, AT4G35510, AT4G35530, AT4G35725, AT4G35940, AT4G35980, AT4G35987, AT4G36100, AT4G36105, AT4G36170, AT4G36370, AT4G36440, AT4G36460, AT4G36500, AT4G36510, AT4G36515, AT4G36520, AT4G36560, AT4G36830, AT4G36925, AT4G36980, AT4G37030, AT4G37090, AT4G37110, AT4G37130, AT4G37240, AT4G37290, AT4G37295, AT4G37300, AT4G37440, AT4G37445, AT4G37450, AT4G37685, AT4G37700, AT4G37740, AT4G37810, AT4G37820, AT4G37920, AT4G37925, AT4G38060, AT4G38070, AT4G38080, AT4G38100, AT4G38120, AT4G38225, AT4G38280, AT4G38330, AT4G38490, AT4G38500, AT4G38680, AT4G38750, AT4G38760, AT4G38820, AT4G38980, AT4G39190, AT4G39235, AT4G39300, AT4G39320, AT4G39360, AT4G39380, AT4G39403, AT4G39420, AT4G39430, AT4G39440, AT4G39450, AT4G39610, AT4G39630, AT4G39670, AT4G39675, AT4G39690, AT4G39745, AT4G39750, AT4G39790, AT4G39840, AT4G39860, AT4G39900, AT4G39917, AT4G39920, AT4G39930, AT4G40020, AT4G40045, AT4G40090, AT5G01015, AT5G01030, AT5G01075, AT5G01080, AT5G01225, AT5G01280, AT5G01350, AT5G01370, AT5G01570, AT5G01690, AT5G01730, AT5G01790, AT5G01840, AT5G01881, AT5G01910, AT5G01970, AT5G02000, AT5G02020, AT5G02090, AT5G02120, AT5G02160, AT5G02200, AT5G02220, AT5G02390, AT5G02420, AT5G02440, AT5G02502, AT5G02510, AT5G02520, AT5G02550, AT5G02640, AT5G02650, AT5G02660, AT5G02680, AT5G02690, AT5G02720, AT5G02740, AT5G02770, AT5G02850, AT5G03050, AT5G03060, AT5G03090, AT5G03110, AT5G03120, AT5G03130, AT5G03210, AT5G03345, AT5G03400, AT5G03420, AT5G03440, AT5G03460, AT5G03545, AT5G03550, AT5G03560, AT5G03670, AT5G03710, AT5G03740, AT5G03750, AT5G03830, AT5G03890, AT5G03900, AT5G03920, AT5G03930, AT5G03950, AT5G03990, AT5G04000, AT5G04030, AT5G04045, AT5G04080, AT5G04090, AT5G04190, AT5G04290, AT5G04470, AT5G04520, AT5G04650, AT5G04670, AT5G04730, AT5G04750, AT5G04790, AT5G04840, AT5G04860, AT5G04910, AT5G05020, AT5G05180, AT5G05190, AT5G05220, AT5G05240, AT5G05250, AT5G05300, AT5G05310, AT5G05360, AT5G05480, AT5G05640, AT5G05660, AT5G05800, AT5G05840, AT5G05930, AT5G05950, AT5G05965, AT5G06010, AT5G06043, AT5G06190, AT5G06240, AT5G06265, AT5G06270, AT5G06280, AT5G06380, AT5G06590, AT5G06610, AT5G06710, AT5G06790, AT5G06890, AT5G06930, AT5G06980, AT5G06990, AT5G07020, AT5G07170, AT5G07330, AT5G07380, AT5G07490, AT5G07570, AT5G07730, AT5G07790, AT5G07890, AT5G07940, AT5G07950, AT5G07970, AT5G07980, AT5G08010, AT5G08040, AT5G08055, AT5G08060, AT5G08090, AT5G08120, AT5G08150, AT5G08185, AT5G08210, AT5G08220, AT5G08240, AT5G08270, AT5G08315, AT5G08320, AT5G08400, AT5G08450, AT5G08505, AT5G08540, AT5G08770, AT5G09225, AT5G09270, AT5G09310, AT5G09390, AT5G09480, AT5G09520, AT5G09530, AT5G09670, AT5G09860, AT5G09960, AT5G09980, AT5G09990, AT5G09995, AT5G10010, AT5G10040, AT5G10110, AT5G10310, AT5G10320, AT5G10430, AT5G10590, AT5G10660, AT5G10670, AT5G10680, AT5G10700, AT5G10710, AT5G10745, AT5G10850, AT5G10890, AT5G10950, AT5G11030, AT5G11070, AT5G11090, AT5G11120, AT5G11220, AT5G11280, AT5G11390, AT5G11420, AT5G11530, AT5G11600, AT5G11630, AT5G11680, AT5G11760, AT5G11780, AT5G11810, AT5G11830, AT5G11870, AT5G11970, AT5G11990, AT5G12010, AT5G12050, AT5G12160, AT5G12170, AT5G12230, AT5G12235, AT5G12240, AT5G12290, AT5G12340, AT5G12360, AT5G12430, AT5G12470, AT5G12880, AT5G12930, AT5G12990, AT5G13090, AT5G13240, AT5G13250, AT5G13260, AT5G13310, AT5G13340, AT5G13390, AT5G13470, AT5G13500, AT5G13540, AT5G13560, AT5G13590, AT5G13610, AT5G13620, AT5G13655, AT5G13660, AT5G13825, AT5G13880, AT5G13940, AT5G13950, AT5G13970, AT5G14020, AT5G14090, AT5G14105, AT5G14110, AT5G14150, AT5G14210, AT5G14290, AT5G14330, AT5G14380, AT5G14410, AT5G14560, AT5G14690, AT5G14710, AT5G14730, AT5G14920, AT5G14930, AT5G14970, AT5G14990, AT5G15000, AT5G15190, AT5G15260, AT5G15320, AT5G15360, AT5G15420, AT5G15560, AT5G15600, AT5G15725, AT5G15780, AT5G15802, AT5G15960, AT5G15970, AT5G15990, AT5G16030, AT5G16060, AT5G16100, AT5G16110, AT5G16160, AT5G16200, AT5G16250, AT5G16453, AT5G16470, AT5G16486, AT5G16520, AT5G16550, AT5G16610, AT5G16660, AT5G16730, AT5G16940, AT5G16950, AT5G17070, AT5G17130, AT5G17160, AT5G17190, AT5G17280, AT5G17340, AT5G17360, AT5G17460, AT5G17510, AT5G17520, AT5G17590, AT5G17610, AT5G17650, AT5G17870, AT5G17910, AT5G18130, AT5G18150, AT5G18250, AT5G18310, AT5G18403, AT5G18407, AT5G18420, AT5G18440, AT5G18540, AT5G18636, AT5G18690, AT5G18710, AT5G18720, AT5G18730, AT5G18740, AT5G18850, AT5G18880, AT5G19070, AT5G19172, AT5G19190, AT5G19230, AT5G19260, AT5G19315, AT5G19340, AT5G19480, AT5G19540, AT5G19570, AT5G19710, AT5G19800, AT5G19810, AT5G19875, AT5G19900, AT5G19950, AT5G19970, AT5G19980, AT5G20045, AT5G20100, AT5G20120, AT5G20130, AT5G20170, AT5G20200, AT5G20370, AT5G20450, AT5G20460, AT5G20610, AT5G20635, AT5G20760, AT5G20770, AT5G20790, AT5G20820, AT5G20935, AT5G21020, AT5G21050, AT5G21070, AT5G21080, AT5G21110, AT5G21125, AT5G21280, AT5G21910, AT5G21940, AT5G22040, AT5G22090, AT5G22120, AT5G22150, AT5G22160, AT5G22170, AT5G22180, AT5G22190, AT5G22210, AT5G22270, AT5G22280, AT5G22310, AT5G22340, AT5G22390, AT5G22430, AT5G22450, AT5G22520, AT5G22530, AT5G22545, AT5G22555, AT5G22650, AT5G22680, AT5G22790, AT5G22875, AT5G22970, AT5G23035, AT5G23100, AT5G23110, AT5G23160, AT5G23180, AT5G23200, AT5G23212, AT5G23390, AT5G23410, AT5G23460, AT5G23490, AT5G23510, AT5G23610, AT5G23640, AT5G23700, AT5G23890, AT5G23920, AT5G24060, AT5G24130, AT5G24165, AT5G24250, AT5G24310, AT5G24313, AT5G24314, AT5G24316, AT5G24355, AT5G24450, AT5G24480, AT5G24500, AT5G24570, AT5G24590, AT5G24610, AT5G24630, AT5G24640, AT5G24655, AT5G24690, AT5G24740, AT5G24860, AT5G24880, AT5G24890, AT5G24920, AT5G24980, AT5G25070, AT5G25250, AT5G25200, AT5G25210, AT5G25240, AT5G25250, AT5G25260, AT5G25265, AT5G25270, AT5G25280, AT5G25360, AT5G25425, AT5G25460, AT5G25500, AT5G25570, AT5G25580, AT5G25590, AT5G25600, AT5G25750, AT5G25754, AT5G25757, AT5G25870, AT5G25920, AT5G26020, AT5G26070, AT5G26080, AT5G26100, AT5G26160, AT5G26230, AT5G26270, AT5G26350, AT5G26620, AT5G26622, AT5G26640, AT5G26650, AT5G26692, AT5G26717, AT5G26720, AT5G26731, AT5G26760, AT5G26770, AT5G26790, AT5G26800, AT5G26805, AT5G26820, AT5G26840, AT5G26850, AT5G26890, AT5G26970, AT5G27020, AT5G27170, AT5G27180, AT5G27210, AT5G27260, AT5G27290, AT5G27330, AT5G27340, AT5G27440, AT5G27500, AT5G27590, AT5G27606, AT5G27710, AT5G27730, AT5G27760, AT5G27800, AT5G27860, AT5G27890, AT5G27940, AT5G27990, AT5G28070, AT5G28090, AT5G28110, AT5G28120, AT5G28130, AT5G28140, AT5G28170, AT5G28190, AT5G28240, AT5G28270, AT5G28295, AT5G28320, AT5G28400, AT5G28410, AT5G28420, AT5G28430, AT5G28440, AT5G28463, AT5G28480, AT5G28482, AT5G28484, AT5G28490, AT5G28500, AT5G28550, AT5G28560, AT5G28600, AT5G28610, AT5G28615, AT5G28620, AT5G28623, AT5G28630, AT5G28720, AT5G28730, AT5G28785, AT5G28790, AT5G28800, AT5G28810, AT5G28820, AT5G28823, AT5G28860, AT5G28910, AT5G28920, AT5G28950, AT5G28960, AT5G28990, AT5G29020, AT5G29050, AT5G29070, AT5G29090, AT5G29210, AT5G29576, AT5G29602, AT5G29613, AT5G30341, AT5G30495, AT5G30520, AT5G31685, AT5G31752, AT5G31753, AT5G31787, AT5G31838, AT5G31873, AT5G32161, AT5G32169, AT5G32312, AT5G32405, AT5G32410, AT5G32590, AT5G32600, AT5G32605, AT5G32610, AT5G32619, AT5G32621, AT5G32775, AT5G33230, AT5G33300, AT5G33303, AT5G33355, AT5G33380, AT5G33390, AT5G33393, AT5G33715, AT5G33806, AT5G33898, AT5G34358, AT5G34450, AT5G34540, AT5G34581, AT5G34820, AT5G34830, AT5G34838, AT5G34860, AT5G34881, AT5G34883, AT5G34887, AT5G34905, AT5G34910, AT5G34970, AT5G34980, AT5G35010, AT5G35020, AT5G35035, AT5G35080, AT5G35090, AT5G35110, AT5G35120, AT5G35195, AT5G35230, AT5G35270, AT5G35290, AT5G35300, AT5G35320, AT5G35460, AT5G35470, AT5G35475, AT5G35480, AT5G35490, AT5G35510, AT5G35603, AT5G35540, AT5G35604, AT5G35646, AT5G35695, AT5G35732, AT5G35737, AT5G35753, AT5G35760, AT5G35792, AT5G35870, AT5G35880, AT5G35890, AT5G35945, AT5G36001, AT5G36020, AT5G36035, AT5G36040, AT5G36060, AT5G36070, AT5G36080, AT5G36100, AT5G36190, AT5G36228, AT5G36280, AT5G36650, AT5G36690, AT5G36710, AT5G36720, AT5G36735, AT5G36780, AT5G36800, AT5G36810, AT5G36900, AT5G36920, AT5G36925, AT5G36960, AT5G37010, AT5G37050, AT5G37120, AT5G37190, AT5G37240, AT5G37360, AT5G37385, AT5G37473, AT5G37474, AT5G37475, AT5G37478, AT5G37480, AT5G37550, AT5G37730, AT5G37840, AT5G37880, AT5G38050, AT5G38060, AT5G38080, AT5G38090, AT5G38190, AT5G38300, AT5G38310, AT5G38317, AT5G38320, AT5G38330, AT5G38380, AT5G38400, AT5G38595, AT5G38660, AT5G38720, AT5G38750, AT5G38770, AT5G38790, AT5G38880, AT5G38980, AT5G39140, AT5G39170, AT5G39200, AT5G39205, AT5G39210, AT5G39240, AT5G39365, AT5G39520, AT5G39530, AT5G39570, AT5G39600, AT5G39790, AT5G39800, AT5G39880, AT5G40070, AT5G40080, AT5G40110, AT5G40155, AT5G40180, AT5G40450, AT5G40460, AT5G40500, AT5G40520, AT5G40595, AT5G40600, AT5G40620, AT5G40640, AT5G40690, AT5G40700, AT5G40710, AT5G40730, AT5G40740, AT5G40800, AT5G40855, AT5G40900, AT5G40960, AT5G40970, AT5G40980, AT5G41020, AT5G41100, AT5G41110, AT5G41140, AT5G41190, AT5G41270, AT5G41320, AT5G41505, AT5G41560, AT5G41620, AT5G41640, AT5G41660, AT5G41780, AT5G41790, AT5G41810, AT5G41860, AT5G41910, AT5G41960, AT5G41980, AT5G42030, AT5G42060, AT5G42070, AT5G42110, AT5G42146, AT5G42223, AT5G42232, AT5G42235, AT5G42242, AT5G42290, AT5G42330, AT5G42530, AT5G42635, AT5G42660, AT5G42710, AT5G42750, AT5G42765, AT5G42780, AT5G42785, AT5G42797, AT5G42825, AT5G42900, AT5G42920, AT5G42955, AT5G42957, AT5G42960, AT5G43000, AT5G43070, AT5G43150, AT5G43185, AT5G43230, AT5G43260, AT5G43285, AT5G43310, AT5G43401, AT5G43405, AT5G43480, AT5G43490, AT5G43510, AT5G43513, AT5G43720, AT5G43750, AT5G43770, AT5G43880, AT5G43970, AT5G44005, AT5G44010, AT5G44040, AT5G44060, AT5G44150, AT5G44313, AT5G44350, AT5G44565, AT5G44570, AT5G44575, AT5G44580, AT5G44650, AT5G44660, AT5G44780, AT5G44820, AT5G44860, AT5G44880, AT5G44973, AT5G45113, AT5G45330, AT5G45350, AT5G45410, AT5G45460, AT5G45573, AT5G45660, AT5G45710, AT5G45740, AT5G45830, AT5G46020, AT5G46115, AT5G46120, AT5G46220, AT5G46295, AT5G46300, AT5G46310, AT5G46320, AT5G46440, AT5G46500, AT5G46620, AT5G46730, AT5G46770, AT5G46795, AT5G46871, AT5G46873, AT5G46874, AT5G46877, AT5G47090, AT5G47110, AT5G47170, AT5G47400, AT5G47410, AT5G47455, AT5G47480, AT5G47490, AT5G47570, AT5G47580, AT5G47635, AT5G47830, AT5G47870, AT5G47920, AT5G47940, AT5G48080, AT5G48175, AT5G48200, AT5G48205, AT5G48210, AT5G48280, AT5G48310, AT5G48335, AT5G48340, AT5G48420, AT5G48470, AT5G48500, AT5G48515, AT5G48520, AT5G48530, AT5G48595, AT5G48605, AT5G48610, AT5G48657, AT5G48720, AT5G48790, AT5G48830, AT5G48860, AT5G48920, AT5G48953, AT5G49015, AT5G49090, AT5G49100, AT5G49110, AT5G49170, AT5G49210, AT5G49250, AT5G49260, AT5G49280, AT5G49380, AT5G49400, AT5G49410, AT5G49440, AT5G49525, AT5G49550, AT5G49590, AT5G49640, AT5G49670, AT5G49680, AT5G49710, AT5G49790, AT5G49830, AT5G49900, AT5G50090, AT5G50175, AT5G50190, AT5G50200, AT5G50290, AT5G50335, AT5G50350, AT5G50360, AT5G50375, AT5G50410, AT5G50420, AT5G50500, AT5G50540, AT5G50560, AT5G50565, AT5G50610, AT5G50645, AT5G50660, AT5G50665, AT5G50710, AT5G50830, AT5G50840, AT5G50880, AT5G50910, AT5G51090, AT5G51105, AT5G51170, AT5G51195, AT5G51200, AT5G51230, AT5G51330, AT5G51390, AT5G51420, AT5G51430, AT5G51510, AT5G51530, AT5G51545, AT5G51580, AT5G51650, AT5G51680, AT5G51840, AT5G51845, AT5G51850, AT5G51960, AT5G52065, AT5G52080, AT5G52110, AT5G52130, AT5G52140, AT5G52200, AT5G52220, AT5G52280, AT5G52290, AT5G52310, AT5G52410, AT5G52420, AT5G52430, AT5G52500, AT5G52530, AT5G52547, AT5G52550, AT5G52580, AT5G52605, AT5G52780, AT5G52800, AT5G52870, AT5G52890, AT5G52900, AT5G52950, AT5G52960, AT5G52965, AT5G52970, AT5G52975, AT5G52980, AT5G53020, AT5G53030, AT5G53045, AT5G53110, AT5G53220, AT5G53280, AT5G53410, AT5G53440, AT5G53620, AT5G53650, AT5G53660, AT5G53670, AT5G53690, AT5G53710, AT5G53740, AT5G53800, AT5G53860, AT5G53880, AT5G53895, AT5G53900, AT5G53905, AT5G53930, AT5G53960, AT5G54062, AT5G54067, AT5G54095, AT5G54145, AT5G54150, AT5G54215, AT5G54350, AT5G54410, AT5G54440, AT5G54460, AT5G54480, AT5G54540, AT5G54585, AT5G54790, AT5G54850, AT5G54870, AT5G54930, AT5G54950, AT5G54970, AT5G55010, AT5G55030, AT5G55060, AT5G55120, AT5G55131, AT5G55132, AT5G55135, AT5G55210, AT5G55330, AT5G55340, AT5G55350, AT5G55360, AT5G55370, AT5G55420, AT5G55430, AT5G55490, AT5G55500, AT5G55507, AT5G55610, AT5G55620, AT5G55640, AT5G55650, AT5G55660, AT5G55680, AT5G55710, AT5G55750, AT5G55790, AT5G55820, AT5G55870, AT5G55893, AT5G55980, AT5G56070, AT5G56075, AT5G56100, AT5G56120, AT5G56170, AT5G56210, AT5G56240, AT5G56250, AT5G56368, AT5G56369, AT5G56520, AT5G56540, AT5G56550, AT5G56770, AT5G56780, AT5G56795, AT5G56850, AT5G56880, AT5G57000, AT5G57060, AT5G57070, AT5G57080, AT5G57180, AT5G57310, AT5G57340, AT5G57345, AT5G57370, AT5G57400, AT5G57410, AT5G57420, AT5G57460, AT5G57500, AT5G57510, AT5G57650, AT5G57685, AT5G57730, AT5G57760, AT5G57790, AT5G57880, AT5G57887, AT5G57910, AT5G58100, AT5G58110, AT5G58210, AT5G58250, AT5G58260, AT5G58360, AT5G58375, AT5G58470, AT5G58500, AT5G58510, AT5G58570, AT5G58630, AT5G58650, AT5G58790, AT5G58880, AT5G58920, AT5G58960, AT5G59050, AT5G59060, AT5G59080, AT5G59105, AT5G59110, AT5G59170, AT5G59210, AT5G59305, AT5G59330, AT5G59350, AT5G59360, AT5G59460, AT5G59500, AT5G59613, AT5G59616, AT5G59830, AT5G59960, AT5G60000, AT5G60030, AT5G60150, AT5G60210, AT5G60240, AT5G60260, AT5G60290, AT5G60330, AT5G60350, AT5G60400, AT5G60430, AT5G60553, AT5G60630, AT5G60650, AT5G60805, AT5G60810, AT5G60840, AT5G60880, AT5G61040, AT5G61090, AT5G61110, AT5G61120, AT5G61200, AT5G61300, AT5G61340, AT5G61360, AT5G61490, AT5G61605, AT5G61630, AT5G61660, AT5G61710, AT5G61865, AT5G61920, AT5G61940, AT5G61950, AT5G61970, AT5G62090, AT5G62140, AT5G62170, AT5G62240, AT5G62270, AT5G62330, AT5G62400, AT5G62440, AT5G62550, AT5G62575, AT5G62623, AT5G62627, AT5G62640, AT5G62750, AT5G62760, AT5G62900, AT5G62960, AT5G63000, AT5G63040, AT5G63050, AT5G63135, AT5G63320, AT5G63340, AT5G63350, AT5G63500, AT5G63540, AT5G63550, AT5G63720, AT5G63740, AT5G63820, AT5G63830, AT5G63905, AT5G64010, AT5G64090, AT5G64130, AT5G64160, AT5G64170, AT5G64180, AT5G64190, AT5G64230, AT5G64310, AT5G64400, AT5G64480, AT5G64510, AT5G64520, AT5G64540, AT5G64550, AT5G64680, AT5G64690, AT5G64770, AT5G64780, AT5G64800, AT5G64816, AT5G64820, AT5G64850, AT5G64870, AT5G64880, AT5G64890, AT5G64900, AT5G64905, AT5G64930, AT5G65120, AT5G65180, AT5G65207, AT5G65250, AT5G65300, AT5G65340, AT5G65390, AT5G65480, AT5G65495, AT5G65540, AT5G65580, AT5G65610, AT5G65660, AT5G65770, AT5G65810, AT5G65880, AT5G65925, AT5G66000, AT5G66030, AT5G66052, AT5G66230, AT5G66250, AT5G66290, AT5G66340, AT5G66440, AT5G66480, AT5G66490, AT5G66580, AT5G66640, AT5G66658, AT5G66740, AT5G66780, AT5G66800, AT5G66815, AT5G66820, AT5G66985, AT5G67020, AT5G67245, AT5G67350, AT5G67390, AT5G67410, AT5G67550, AT5G67600, AT5G67610, AT5G67620, AT5G67640, ATCG00870, ATCG01270, ATMG00010, ATMG00030, ATMG00050, ATMG00120, ATMG00130, ATMG00150, ATMG00170, ATMG00180, ATMG00200, ATMG00260, ATMG00300, ATMG00310, ATMG00320, ATMG00400, ATMG00430, ATMG00440, ATMG00450, ATMG00470, ATMG00500, ATMG00530, ATMG00540, ATMG00550, ATMG00600, ATMG00610, ATMG00620, ATMG00630, ATMG00660, ATMG00670, ATMG00680, ATMG00720, ATMG00740, ATMG00750, ATMG00760, ATMG00770, ATMG00840, ATMG00870, ATMG00880, ATMG00890, ATMG00910, ATMG00920, ATMG00970, ATMG01000, ATMG01010, ATMG01020, ATMG01030, ATMG01040, ATMG01050, ATMG01060, ATMG01090, ATMG01100, ATMG01130, ATMG01140, ATMG01150, ATMG01180, ATMG01200, ATMG01210, ATMG01220, ATMG01230, ATMG01240, ATMG01260, ATMG01290, ATMG01300, ATMG01310, ATMG01330, ATMG01350, ATMG01370, and ATMG01400. With regard to the POFs identified in *Arabidopsis*, the following POFs were identified as specific either to a single species or a single genus (referred to herein as ssPOFs): Locus ID AT1G01400, AT1G01810, AT1G01990, AT1G02320, AT1G02350, AT1G02405, AT1G02450, AT1G02490, AT1G02540, AT1G02710, AT1G02965, AT1G03106, AT1G03200, AT1G03240, AT1G03320, AT1G03420, AT1G03660, AT1G04660, AT1G04670, AT1G04800, AT1G05040, AT1G05065, AT1G05085, AT1G05330, AT1G05340, AT1G05450, AT1G05490, AT1G05575, AT1G06135, AT1G06320, AT1G06420, AT1G06475, AT1G06930, AT1G07135, AT1G07190, AT1G07473, AT1G07500, AT1G07680, AT1G07690, AT1G08035, AT1G09415, AT1G10100, AT1G10420, AT1G10990, AT1G11470, AT1G11850, AT1G12080, AT1G12660, AT1G12805, AT1G12810, AT1G12845, AT1G13605, AT1G13607, AT1G13608, AT1G13609, AT1G13620, AT1G13670, AT1G13755, AT1G14755, AT1G15385, AT1G15757, AT1G15825, AT1G15830, AT1G15840, AT1G16025, AT1G16515, AT1G16730, AT1G17090,
AT1G17285, AT1G17300, AT1G17510, AT1G17780,
AT1G17900, AT1G18220, AT1G18510, AT1G19394,
AT1G19397, AT1G19500, AT1G19620, AT1G19960,
AT1G20070, AT1G20100, AT1G20280, AT1G20690,
AT1G21020, AT1G21323, AT1G21395, AT1G21475,
AT1G21520, AT1G21940, AT1G21950, AT1G22010,
AT1G22120, AT1G22140, AT1G22335, AT1G22590,
AT1G22885, AT1G22890, AT1G23050, AT1G23650,
AT1G24060, AT1G24145, AT1G24390, AT1G24575,
AT1G24822, AT1G24851, AT1G24938, AT1G24996,
AT1G25025, AT1G25097, AT1G25112, AT1G25170,
AT1G25180, AT1G25425, AT1G26140, AT1G26210,
AT1G26290, AT1G26350, AT1G26710, AT1G26720,
AT1G27550, AT1G27610, AT1G27640, AT1G27670,
AT1G27695, AT1G27710, AT1G27790, AT1G28135,
AT1G28375, AT1G28630, AT1G29010, AT1G29179,
AT1G29355, AT1G29480, AT1G29530, AT1G29540,
AT1G29560, AT1G29580, AT1G29610, AT1G29620,
AT1G30250, AT1G30515, AT1G30757, AT1G30795,
AT1G30814, AT1G30835, AT1G31060, AT1G31150,
AT1G31270, AT1G31335, AT1G31520, AT1G31580,
AT1G31620, AT1G31750, AT1G31772, AT1G31835,
AT1G31960, AT1G31990, AT1G32000, AT1G32010,
AT1G32040, AT1G32290, AT1G32337, AT1G32570,
AT1G32630, AT1G32650, AT1G32670, AT1G32680,
AT1G32920, AT1G32928, AT1G32975, AT1G33135,
AT1G33607, AT1G33640, AT1G33820, AT1G33860,
AT1G34047, AT1G34095, AT1G34280, AT1G34315,
AT1G34400, AT1G34440, AT1G34590, AT1G34730,
AT1G34910, AT1G35030, AT1G35040, AT1G35080,
AT1G35100, AT1G35183, AT1G35230, AT1G35320,
AT1G35375, AT1G35435, AT1G35500, AT1G35513,
AT1G35614, AT1G35617, AT1G35640, AT1G35820,
AT1G35880, AT1G35890, AT1G35900, AT1G36100,
AT1G36230, AT1G36395, AT1G36640, AT1G36670,
AT1G36675, AT1G36745, AT1G36756, AT1G36763,
AT1G36925, AT1G36960, AT1G36970, AT1G37000,
AT1G37015, AT1G37037, AT1G37045, AT1G38380,
AT1G38630, AT1G38790, AT1G38950, AT1G39350,
AT1G40080, AT1G40115, AT1G40125, AT1G40129,
AT1G40133, AT1G40230, AT1G41650, AT1G41750,
AT1G41770, AT1G41810, AT1G41820, AT1G41855,
AT1G41870, AT1G41900, AT1G42080, AT1G42190,
AT1G42367, AT1G42393, AT1G42515, AT1G42580,
AT1G42630, AT1G42700, AT1G42740, AT1G43205,
AT1G43230, AT1G43320, AT1G43415, AT1G43720,
AT1G43777, AT1G43810, AT1G43920, AT1G43940,
AT1G43970, AT1G44085, AT1G44222, AT1G44740,
AT1G44850, AT1G44875, AT1G44930, AT1G44990,
AT1G45165, AT1G45403, AT1G46336, AT1G47280,
AT1G47317, AT1G47395, AT1G47400, AT1G47485,
AT1G47495, AT1G47660, AT1G47680, AT1G47690,
AT1G47700, AT1G47770, AT1G47813, AT1G48145,
AT1G48250, AT1G48325, AT1G48730, AT1G49110,
AT1G49150, AT1G49500, AT1G49680, AT1G49715,
AT1G49940, AT1G50080, AT1G50220, AT1G50290,
AT1G50350, AT1G50530, AT1G50800, AT1G50930,
AT1G51000, AT1G51010, AT1G51030, AT1G51430,
AT1G51915, AT1G51970, AT1G52087, AT1G52090,
AT1G52390, AT1G52410, AT1G52550, AT1G52615,
AT1G52827, AT1G52840, AT1G52905, AT1G53265,
AT1G53285, AT1G53480, AT1G53610, AT1G53620,
AT1G53625, AT1G53640, AT1G53785, AT1G53935,
AT1G53970, AT1G54420, AT1G54445, AT1G54575,
AT1G54640, AT1G54720, AT1G54880, AT1G54923,
AT1G54926, AT1G54950, AT1G55220, AT1G55330,
AT1G55400, AT1G55675, AT1G55710, AT1G55990,
AT1G56085, AT1G56270, AT1G56415, AT1G56530,
AT1G56553, AT1G56555, AT1G56660, AT1G58055,
AT1G58150, AT1G58225, AT1G58235, AT1G58242,
AT1G59535, AT1G59722, AT1G59865, AT1G59885,
AT1G60240, AT1G60983, AT1G60987, AT1G61090,
AT1G61095, AT1G61097, AT1G61200, AT1G61688,
AT1G61920, AT1G62000, AT1G62060, AT1G62070,
AT1G62080, AT1G62210, AT1G62220, AT1G62225,
AT1G62240, AT1G62480, AT1G62690, AT1G62935,
AT1G63055, AT1G63105, AT1G63240, AT1G63522,
AT1G63535, AT1G63960, AT1G64107, AT1G64360,
AT1G64370, AT1G64405, AT1G64490, AT1G64560,
AT1G64800, AT1G65342, AT1G65352, AT1G65490,
AT1G65500, AT1G65510, AT1G65845, AT1G66145,
AT1G66245, AT1G66790, AT1G66820, AT1G67350,
AT1G67670, AT1G67775, AT1G67855, AT1G67860,
AT1G67865, AT1G67870, AT1G68250, AT1G68430,
AT1G68725, AT1G68845, AT1G68870, AT1G68875,
AT1G68905, AT1G68907, AT1G68935, AT1G68945,
AT1G69050, AT1G69470, AT1G69760, AT1G69825,
AT1G69970, AT1G70350, AT1G70470, AT1G70895,
AT1G70990, AT1G71235, AT1G71470, AT1G71910,
AT1G72080, AT1G72580, AT1G72600, AT1G72645,
AT1G73130, AT1G73177, AT1G73510, AT1G73603,
AT1G73607, AT1G74045, AT1G74055, AT1G75190,
AT1G75770, AT1G75870, AT1G76230, AT1G76820,
AT1G76840, AT1G76910, AT1G76955, AT1G76960,
AT1G76965, AT1G77655, AT1G77765, AT1G77885,
AT1G77910, AT1G77960, AT1G78030, AT1G79170,
AT1G80610, AT1G80865, AT2G01031, AT2G01175,
AT2G01310, AT2G01400, AT2G02280, AT2G02440,
AT2G02490, AT2G02515, AT2G02795, AT2G02835,
AT2G02840, AT2G03180, AT2G03310, AT2G03320,
AT2G03540, AT2G03570, AT2G03580, AT2G03830,
AT2G03932, AT2G03937, AT2G04000, AT2G04025,
AT2G04034, AT2G04045, AT2G04046, AT2G04063,
AT2G04320, AT2G04370, AT2G04380, AT2G04410,
AT2G04515, AT2G04600, AT2G04675, AT2G04800,
AT2G04870, AT2G04925, AT2G05000, AT2G05117,
AT2G05185, AT2G05270, AT2G05350, AT2G05500,
AT2G05564, AT2G05645, AT2G05647, AT2G05752,
AT2G05915, AT2G06095, AT2G06140, AT2G06166,
AT2G06230, AT2G06390, AT2G06420, AT2G06480,
AT2G06555, AT2G06570, AT2G06620, AT2G06630,
AT2G06645, AT2G06750, AT2G06775, AT2G06906,
AT2G06908, AT2G06914, AT2G07000, AT2G07190,
AT2G07215, AT2G07280, AT2G07290, AT2G07310,
AT2G07505, AT2G07669, AT2G07672, AT2G07673,
AT2G07674, AT2G07676, AT2G07678, AT2G07691,
AT2G07692, AT2G07701, AT2G07702, AT2G07705,
AT2G07706, AT2G07708, AT2G07710, AT2G07713,
AT2G07719, AT2G07721, AT2G07724, AT2G07728,
AT2G07738, AT2G07772, AT2G07774, AT2G07775,
AT2G07776, AT2G07777, AT2G07779, AT2G07787,
AT2G07795, AT2G07880, AT2G07981, AT2G08986,
AT2G09388, AT2G09840, AT2G09865, AT2G09900,
AT2G10020, AT2G10105, AT2G10110, AT2G10175,
AT2G10285, AT2G10340, AT2G10360, AT2G10380,
AT2G10390, AT2G10470, AT2G10550, AT2G10555,
AT2G10602, AT2G10608, AT2G10850, AT2G10870,
AT2G10920, AT2G10930, AT2G10965, AT2G10975,
AT2G11005, AT2G11015, AT2G11090, AT2G11135,
AT2G11370, AT2G11405, AT2G11462, AT2G11570,
AT2G11620, AT2G11626, AT2G11775, AT2G11910,
AT2G12110, AT2G12120, AT2G12130, AT2G12170,
AT2G12320, AT2G12405, AT2G12465, AT2G12475, AT2G12505, AT2G12610, AT2G12685, AT2G12700, AT2G12875, AT2G12905, AT2G12935, AT2G12945, AT2G13125, AT2G13126, AT2G13270, AT2G13320, AT2G13430, AT2G13500, AT2G13510, AT2G13550, AT2G13660, AT2G13730, AT2G13760, AT2G13865, AT2G13975, AT2G14000, AT2G14020, AT2G14240, AT2G14247, AT2G14340, AT2G14390, AT2G14460, AT2G14590, AT2G14600, AT2G14700, AT2G14774, AT2G14800, AT2G14810, AT2G14890, AT2G14935, AT2G15185, AT2G15327, AT2G15340, AT2G15345, AT2G15420, AT2G15535, AT2G15550, AT2G15600, AT2G15800, AT2G15815, AT2G15830, AT2G15930, AT2G15960, AT2G16015, AT2G16020, AT2G16170, AT2G16340, AT2G16410, AT2G16575, AT2G16586, AT2G16676, AT2G16820, AT2G17442, AT2G17540, AT2G17723, AT2G17960, AT2G18070, AT2G18200, AT2G18270, AT2G18440, AT2G18610, AT2G18920, AT2G18930, AT2G18970, AT2G19200, AT2G19290, AT2G19300, AT2G19320, AT2G19420, AT2G19700, AT2G19802, AT2G19850, AT2G19893, AT2G20150, AT2G20208, AT2G20250, AT2G20463, AT2G20595, AT2G20620, AT2G20625, AT2G20870, AT2G20970, AT2G21185, AT2G21237, AT2G21465, AT2G21725, AT2G21780, AT2G22000, AT2G22080, AT2G22121, AT2G22122, AT2G22320, AT2G22340, AT2G22470, AT2G22510, AT2G22520, AT2G22805, AT2G22807, AT2G22820, AT2G22905, AT2G22940, AT2G22941, AT2G23040, AT2G23130, AT2G23440, AT2G23490, AT2G23920, AT2G23985, AT2G24285, AT2G24310, AT2G24340, AT2G24460, AT2G24617, AT2G24625, AT2G24780, AT2G24910, AT2G24945, AT2G25185, AT2G25250, AT2G25510, AT2G25565, AT2G25685, AT2G25990, AT2G26120, AT2G26880, AT2G27250, AT2G27315, AT2G27380, AT2G27390, AT2G27535, AT2G27540, AT2G28330, AT2G28570, AT2G28625, AT2G29045, AT2G29180, AT2G29790, AT2G29920, AT2G29995, AT2G30430, AT2G30560, AT2G30760, AT2G30925, AT2G30930, AT2G30960, AT2G30985, AT2G31035, AT2G31345, AT2G31590, AT2G31700, AT2G31751, AT2G31850, AT2G32275, AT2G32890, AT2G33233, AT2G34010, AT2G34100, AT2G34110, AT2G34120, AT2G34123, AT2G34185, AT2G34220, AT2G34230, AT2G34270, AT2G34310, AT2G34330, AT2G34655, AT2G34800, AT2G34870, AT2G35070, AT2G35080, AT2G35090, AT2G35733, AT2G35750, AT2G35870, AT2G36030, AT2G36040, AT2G36255, AT2G36440, AT2G36695, AT2G36724, AT2G36920, AT2G36940, AT2G37070, AT2G37300, AT2G37910, AT2G38350, AT2G38690, AT2G38823, AT2G39160, AT2G39520, AT2G39680, AT2G40020, AT2G40085, AT2G40530, AT2G40765, AT2G40955, AT2G41230, AT2G41260, AT2G41280, AT2G41390, AT2G41400, AT2G41420, AT2G41440, AT2G41650, AT2G41780, AT2G41905, AT2G42050, AT2G42340, AT2G42395, AT2G42540, AT2G42860, AT2G42955, AT2G43450, AT2G44010, AT2G45403, AT2G45780, AT2G45860, AT2G45930, AT2G46360, AT2G46390, AT2G47200, AT2G47660, AT2G47720, AT2G47950, AT2G48075, AT2G48090, AT3G01230, AT3G01240, AT3G01250, AT3G01323, AT3G01325, AT3G01345, AT3G01700, AT3G01730, AT3G01960, AT3G02240, AT3G02390, AT3G02670, AT3G03020, AT3G04640, AT3G04903, AT3G04943, AT3G05080, AT3G05460, AT3G05727, AT3G05730, AT3G05935, AT3G06090, AT3G06360, AT3G06435, AT3G06545, AT3G06600, AT3G06710, AT3G06750, AT3G06870, AT3G06895, AT3G07005, AT3G07195, AT3G07568, AT3G07710, AT3G09032, AT3G09130, AT3G09162, AT3G09280, AT3G09750, AT3G09922, AT3G10116, AT3G10195, AT3G10525, AT3G10830, AT3G10930, AT3G11060, AT3G11160, AT3G11640, AT3G11745, AT3G11860, AT3G12510, AT3G12840, AT3G12977, AT3G13240, AT3G13370, AT3G13403, AT3G13435, AT3G13500, AT3G13630, AT3G13674, AT3G13845, AT3G13857, AT3G14340, AT3G14395, AT3G14480, AT3G14560, AT3G14670, AT3G15357, AT3G15400, AT3G15440, AT3G15780, AT3G15860, AT3G15910, AT3G16750, AT3G16895, AT3G17155, AT3G17190, AT3G18250, AT3G18485, AT3G18540, AT3G18700, AT3G19030, AT3G19055, AT3G19530, AT3G19790, AT3G20155, AT3G20362, AT3G20555, AT3G20850, AT3G20865, AT3G20900, AT3G21570, AT3G21680, AT3G22070, AT3G22090, AT3G22231, AT3G22235, AT3G22240, AT3G22415, AT3G23040, AT3G23165, AT3G23167, AT3G23172, AT3G23245, AT3G23295, AT3G23715, AT3G23720, AT3G23727, AT3G23850, AT3G24225, AT3G24250, AT3G24280, AT3G24380, AT3G24508, AT3G24510, AT3G24513, AT3G24517, AT3G24640, AT3G24770, AT3G25080, AT3G25200, AT3G25655, AT3G25727, AT3G25882, AT3G25905, AT3G26110, AT3G26235, AT3G26616, AT3G26800, AT3G27025, AT3G27370, AT3G27590, AT3G27800, AT3G27906, AT3G27990, AT3G28110, AT3G28120, AT3G28170, AT3G28190, AT3G28240, AT3G28260, AT3G28280, AT3G28420, AT3G28530, AT3G28590, AT3G29034, AT3G29080, AT3G29140, AT3G29210, AT3G29300, AT3G29305, AT3G29560, AT3G29570, AT3G29600, AT3G29610, AT3G29700, AT3G29786, AT3G29790, AT3G29796, AT3G30150, AT3G30160, AT3G30220, AT3G30250, AT3G30320, AT3G30350, AT3G30360, AT3G30490, AT3G30510, AT3G30520, AT3G30580, AT3G30590, AT3G30610, AT3G30645, AT3G30650, AT3G30660, AT3G30670, AT3G30690, AT3G30700, AT3G30720, AT3G30750, AT3G30751, AT3G30755, AT3G30816, AT3G30820, AT3G30840, AT3G30845, AT3G31300, AT3G31310, AT3G31320, AT3G31330, AT3G31350, AT3G31370, AT3G31400, AT3G31406, AT3G31540, AT3G31910, AT3G31915, AT3G31940, AT3G31955, AT3G32050, AT3G32070, AT3G32100, AT3G32120, AT3G32150, AT3G32160, AT3G32180, AT3G32190, AT3G32200, AT3G32896, AT3G32902, AT3G32903, AT3G32904, AT3G32960, AT3G33064, AT3G33073, AT3G33080, AT3G33131, AT3G33187, AT3G33230, AT3G33293, AT3G33393, AT3G33448, AT3G33494, AT3G33572, AT3G42070, AT3G42090, AT3G42120, AT3G42130, AT3G42140, AT3G42190, AT3G42200, AT3G42240, AT3G42254, AT3G42300, AT3G42310, AT3G42380, AT3G42390, AT3G42430, AT3G42436, AT3G42473, AT3G42480, AT3G42490, AT3G42510, AT3G42520, AT3G42540, AT3G42556, AT3G42590, AT3G42610, AT3G42680, AT3G42700, AT3G42723, AT3G42740, AT3G42750, AT3G42780, AT3G42786, AT3G42810, AT3G42870, AT3G42920, AT3G42970, AT3G42990, AT3G43140, AT3G43150, AT3G43153, AT3G43160, AT3G43280, AT3G43290, AT3G43410, AT3G43420, AT3G43450, AT3G43470, AT3G43480, AT3G43500, AT3G43528, AT3G43580, AT3G43583, AT3G43680, AT3G43682, AT3G43833, AT3G43863, AT3G43870, AT3G43880, AT3G43940, AT3G43970, AT3G44040, AT3G44070, AT3G44140, AT3G44160, AT3G44210, AT3G44230, AT3G44235, AT3G44430, AT3G44440, AT3G44470, AT3G44570, AT3G44580, AT3G44690, AT3G44755, AT3G44760, AT3G44770, AT3G44935, AT3G44950, AT3G44980, AT3G45093, AT3G45110, AT3G45120, AT3G45160, AT3G45230, AT3G45320, AT3G45360, AT3G45370, AT3G45443, AT3G45730, AT3G45820, AT3G45910, AT3G46150, AT3G46360, AT3G46380, AT3G46390, AT3G47100, AT3G47230, AT3G47240, AT3G47295, AT3G47320, AT3G47410, AT3G47510, AT3G47836, AT3G47920, AT3G47965, AT3G48185, AT3G48231, AT3G48640, AT3G49230, AT3G49270, AT3G49300, AT3G49305, AT3G49307, AT3G49540, AT3G49770, AT3G49820, AT3G50250, AT3G50320, AT3G50373, AT3G50540, AT3G50550, AT3G50570, AT3G50580, AT3G50925, AT3G52550, AT3G52700, AT3G53235, AT3G54520, AT3G54530, AT3G54730, AT3G55790, AT3G55860, AT3G55910, AT3G56260, AT3G56390, AT3G56610, AT3G56670, AT3G56910, AT3G57110, AT3G57160, AT3G57210, AT3G57690, AT3G57850, AT3G58080, AT3G58230, AT3G58280, AT3G58300, AT3G58330, AT3G58540, AT3G58770, AT3G58870, AT3G59370, AT3G59460, AT3G59880, AT3G59930, AT3G60560, AT3G60760, AT3G60890, AT3G60930, AT3G61898, AT3G62350, AT3G62400, AT3G62480, AT3G62490, AT3G62990, AT3G63040, AT3G63050, AT3G63100, AT3G63160, AT4G00280, AT4G00890, AT4G00930, AT4G01340, AT4G01525, AT4G01535, AT4G01735, AT4G01895, AT4G01915, AT4G01985, AT4G02000, AT4G02160, AT4G02465, AT4G03165, AT4G03305, AT4G03505, AT4G03580, AT4G03680, AT4G03740, AT4G03750, AT4G03940, AT4G03970, AT4G03975, AT4G03979, AT4G04155, AT4G04273, AT4G04394, AT4G04396, AT4G04398, AT4G04423, AT4G04525, AT4G04730, AT4G04820, AT4G04925, AT4G05290, AT4G05523, AT4G05553, AT4G05560, AT4G05580, AT4G05581, AT4G05616, AT4G05631, AT4G05632, AT4G05636, AT4G05640, AT4G06490, AT4G06603, AT4G06637, AT4G06672, AT4G06716, AT4G06724, AT4G06728, AT4G06735, AT4G06740, AT4G07380, AT4G07452, AT4G07460, AT4G07485, AT4G07500, AT4G07523, AT4G07526, AT4G07666, AT4G07675, AT4G07740, AT4G07825, AT4G07868, AT4G07932, AT4G07943, AT4G07965, AT4G08028, AT4G08039, AT4G08097, AT4G08098, AT4G08111, AT4G08130, AT4G08270, AT4G08336, AT4G08395, AT4G08485, AT4G08555, AT4G08593, AT4G08602, AT4G08710, AT4G08730, AT4G08740, AT4G08760, AT4G08868, AT4G08869, AT4G08874, AT4G08875, AT4G09030, AT4G09153, AT4G09210, AT4G09220, AT4G09260, AT4G09270, AT4G09290, AT4G09390, AT4G09647, AT4G09840, AT4G09850, AT4G09860, AT4G09880, AT4G09984, AT4G10820, AT4G10845, AT4G10860, AT4G10870, AT4G11020, AT4G11100, AT4G11385, AT4G11393, AT4G11700, AT4G11870, AT4G11940, AT4G12005, AT4G12220, AT4G12380, AT4G12580, AT4G12735, AT4G12930, AT4G12940, AT4G12990, AT4G13095, AT4G13150, AT4G13195, AT4G13235, AT4G13320, AT4G13470, AT4G13955, AT4G13968, AT4G14104, AT4G14120, AT4G14315, AT4G14530, AT4G14650, AT4G14810, AT4G15096, AT4G15150, AT4G15460, AT4G15563, AT4G15650, AT4G15710, AT4G15733, AT4G15735, AT4G15950, AT4G15990, AT4G16000, AT4G16040, AT4G16090, AT4G16140, AT4G16215, AT4G16240, AT4G16447, AT4G16460, AT4G16515, AT4G16840, AT4G16980, AT4G17700, AT4G17713, AT4G17930, AT4G17990, AT4G18000, AT4G18080, AT4G18090, AT4G18280, AT4G18310, AT4G18395, AT4G18420, AT4G18490, AT4G18500, AT4G18501, AT4G18510, AT4G18580, AT4G18823, AT4G18850, AT4G18860, AT4G19095, AT4G19200, AT4G19240, AT4G19270, AT4G19280, AT4G19290, AT4G19305, AT4G19320, AT4G19480, AT4G19620, AT4G19905, AT4G20095, AT4G20250, AT4G20290, AT4G20470, AT4G20500, AT4G20510, AT4G20690, AT4G20715, AT4G21215, AT4G21865, AT4G21920, AT4G21950, AT4G22210, AT4G22214, AT4G22217, AT4G22235, AT4G22420, AT4G22430, AT4G22440, AT4G22510, AT4G22800, AT4G23090, AT4G23110, AT4G23493, AT4G23760, AT4G23770, AT4G23780, AT4G23870, AT4G23970, AT4G24030, AT4G24275, AT4G24300, AT4G24410, AT4G24600, AT4G24950, AT4G25510, AT4G26030, AT4G26040, AT4G26290, AT4G26320, AT4G26960, AT4G27415, AT4G27530, AT4G27580, AT4G27652, AT4G27654, AT4G27657, AT4G27850, AT4G27930, AT4G28085, AT4G28160, AT4G28180, AT4G28460, AT4G28810, AT4G28870, AT4G28920, AT4G28930, AT4G29020, AT4G29030, AT4G29200, AT4G29273, AT4G29280, AT4G29285, AT4G29290, AT4G29300, AT4G29305, AT4G30050, AT4G30064, AT4G30450, AT4G30460, AT4G30662, AT4G30670, AT4G30730, AT4G30750, AT4G30970, AT4G31030, AT4G31260, AT4G31280, AT4G31875, AT4G31960, AT4G32080, AT4G32230, AT4G32240, AT4G33310, AT4G33560, AT4G33610, AT4G33660, AT4G33666, AT4G33750, AT4G33960, AT4G34690, AT4G35170, AT4G35400, AT4G35430, AT4G35725, AT4G36170, AT4G36370, AT4G36460, AT4G36510, AT4G36515, AT4G36560, AT4G36925, AT4G37295, AT4G37450, AT4G37685, AT4G38080, AT4G38330, AT4G38820, AT4G39320, AT4G39360, AT4G39403, AT4G39675, AT4G39745, AT4G39917, AT4G39930, AT4G40090, AT5G01080, AT5G01881, AT5G02000, AT5G02520, AT5G02550, AT5G02650, AT5G02690, AT5G03060, AT5G03090, AT5G03130, AT5G03210, AT5G03400, AT5G03545, AT5G03550, AT5G03710, AT5G03920, AT5G03930, AT5G03950, AT5G04030, AT5G04045, AT5G04470, AT5G04650, AT5G04790, AT5G05020, AT5G05640, AT5G05965, AT5G06043, AT5G06190, AT5G06380, AT5G06980, AT5G07730, AT5G08090, AT5G08150, AT5G08185, AT5G08210, AT5G08220, AT5G08505, AT5G09480, AT5G09520, AT5G09980, AT5G09990, AT5G10040, AT5G10430, AT5G10590, AT5G10670, AT5G10745, AT5G11120, AT5G11830, AT5G11990, AT5G12880, AT5G12990, AT5G13825, AT5G14330, AT5G14380, AT5G14560, AT5G14730, AT5G15000, AT5G15190, AT5G15360, AT5G15420, AT5G15560, AT5G15725, AT5G15960, AT5G15970, AT5G15990, AT5G17130, AT5G17340, AT5G17360, AT5G17590, AT5G17650, AT5G18403, AT5G18407, AT5G18690, AT5G19172, AT5G19800, AT5G19810, AT5G20460, AT5G20760, AT5G20770, AT5G21020, AT5G21110, AT5G21125, AT5G21910, AT5G22150, AT5G22160, AT5G22170, AT5G22180, AT5G22190, AT5G22520, AT5G22530, AT5G22545, AT5G22555, AT5G22680, AT5G22970, AT5G23035, AT5G23180, AT5G23212, AT5G23460, AT5G23640, AT5G24250, AT5G24313, AT5G24316, AT5G24480, AT5G24570, AT5G24590, AT5G25000, AT5G25210, AT5G25425, AT5G25600, AT5G25750, AT5G25870, AT5G25920, AT5G26020, AT5G26070, AT5G26080, AT5G26100, AT5G26270, AT5G26350, AT5G26622, AT5G26692, AT5G26717, AT5G26720, AT5G26800, AT5G26840, AT5G26890, AT5G26970, AT5G27170, AT5G27180, AT5G27340, AT5G27440, AT5G27500, AT5G27590, AT5G27606, AT5G27800, AT5G27890, AT5G28070, AT5G28090, AT5G28110, AT5G28120, AT5G28130, AT5G28140, AT5G28170, AT5G28190, AT5G28240, AT5G28270, AT5G28295, AT5G28410, AT5G28430, AT5G28463, AT5G28480, AT5G28482, AT5G28484, AT5G28560, AT5G28600, AT5G28610, AT5G28620, AT5G28623, AT5G28630, AT5G28720, AT5G28785, AT5G28790, AT5G28800, AT5G28810, AT5G28820, AT5G28860, AT5G28920, AT5G28990, AT5G29020, AT5G29050, AT5G29070, AT5G29090, AT5G29210, AT5G29576, AT5G29602, AT5G29613, AT5G30341, AT5G30520, AT5G31685, AT5G31752, AT5G31753, AT5G31787, AT5G31838, AT5G31873, AT5G32161, AT5G32169, AT5G32312, AT5G32405, AT5G32410, AT5G32590, AT5G32600, AT5G32605, AT5G32610, AT5G32619, AT5G32775, AT5G33230, AT5G33355, AT5G33380, AT5G33390, AT5G33393, AT5G33715, AT5G33806, AT5G33898, AT5G34358, AT5G34450, AT5G34581, AT5G34820, AT5G34830, AT5G34910, AT5G34970, AT5G34980, AT5G35010, AT5G35020, AT5G35035, AT5G35090, AT5G35195, AT5G35230, AT5G35270, AT5G35290, AT5G35300, AT5G35470, AT5G35480, AT5G35490, AT5G35510, AT5G35540, AT5G35603, AT5G35604, AT5G35646, AT5G35737, AT5G35760, AT5G35792, AT5G35880, AT5G35890, AT5G35945, AT5G36020, AT5G36035, AT5G36040, AT5G36060, AT5G36070, AT5G36080, AT5G36190, AT5G36650, AT5G36720, AT5G36735, AT5G36900, AT5G36920, AT5G36925, AT5G36960, AT5G37120, AT5G37240, AT5G37385, AT5G37473, AT5G37474, AT5G37880, AT5G38080, AT5G38090, AT5G38190, AT5G38310, AT5G38400, AT5G38595, AT5G38790, AT5G38980, AT5G39140, AT5G39170, AT5G39205, AT5G39365, AT5G39570, AT5G39880, AT5G40070, AT5G40110, AT5G40155, AT5G40180, AT5G40595, AT5G40620, AT5G40730, AT5G40855, AT5G41320, AT5G41640, AT5G41660, AT5G42110, AT5G42146, AT5G42223, AT5G42232, AT5G42235, AT5G42242, AT5G42530, AT5G42635, AT5G42797, AT5G42825, AT5G43000, AT5G43185, AT5G43285, AT5G43401, AT5G43405, AT5G43480, AT5G43510, AT5G43513, AT5G43770, AT5G44005, AT5G44313, AT5G44565, AT5G44570, AT5G44575, AT5G44580, AT5G44880, AT5G44973, AT5G45573, AT5G46115, AT5G46120, AT5G46300, AT5G46310, AT5G46320, AT5G46500, AT5G46730, AT5G46770, AT5G46871, AT5G46873, AT5G46874, AT5G46877, AT5G47170, AT5G48175, AT5G48200, AT5G48280, AT5G48420, AT5G48515, AT5G48530, AT5G48595, AT5G48605, AT5G48657, AT5G48860, AT5G48953, AT5G49015, AT5G49090, AT5G49250, AT5G49260, AT5G49280, AT5G49440, AT5G49590, AT5G49640, AT5G49790, AT5G50190, AT5G50335, AT5G50500, AT5G50540, AT5G50565, AT5G50610, AT5G50645, AT5G50665, AT5G50710, AT5G50880, AT5G50910, AT5G51090, AT5G51105, AT5G51195, AT5G51390, AT5G51580, AT5G51650, AT5G51845, AT5G52080, AT5G52130, AT5G52547, AT5G52965, AT5G53410, AT5G53740, AT5G53895, AT5G53905, AT5G53960, AT5G54067, AT5G54095, AT5G54145, AT5G54215, AT5G54350, AT5G54410, AT5G54460, AT5G54585, AT5G54790, AT5G54970, AT5G55010, AT5G55131, AT5G55132, AT5G55135, AT5G55420, AT5G55430, AT5G55507, AT5G55650, AT5G55680, AT5G55750, AT5G55790, AT5G55870, AT5G55893, AT5G56100, AT5G56368, AT5G56369, AT5G56795, AT5G56880, AT5G57310, AT5G57400, AT5G57650, AT5G57730, AT5G57760, AT5G57790, AT5G57887, AT5G58570, AT5G58650, AT5G59060, AT5G59105, AT5G59170, AT5G59330, AT5G59360, AT5G60000, AT5G60240, AT5G60260, AT5G60290, AT5G60330, AT5G60350, AT5G60400, AT5G60553, AT5G60650, AT5G60805, AT5G60810, AT5G61110, AT5G61120, AT5G61360, AT5G61605, AT5G61660, AT5G61710, AT5G62330, AT5G62400, AT5G62623, AT5G62627, AT5G62750, AT5G63340, AT5G63720, AT5G63820, AT5G63905, AT5G64540, AT5G64690, AT5G64770, AT5G64800, AT5G64890, AT5G64900, AT5G64905, AT5G65300, AT5G65390, AT5G65495, AT5G65580, AT5G65610, AT5G65880, AT5G65925, AT5G66000, AT5G66052, AT5G66340, AT5G66658, AT5G66985, AT5G67245, AT5G67350, AT5G67600, AT5G67640, ATCG00870, ATCG01270, ATMG00030, ATMG00050, ATMG00120, ATMG00130, ATMG00150, ATMG00200, ATMG00260, ATMG00320, ATMG00400, ATMG00430, ATMG00440, ATMG00450, ATMG00470, ATMG00500, ATMG00530, ATMG00540, ATMG00600, ATMG00610, ATMG00630, ATMG00670, ATMG00680, ATMG00720, ATMG00740, ATMG00760, ATMG00770, ATMG00840, ATMG00870, ATMG00880, ATMG00890, ATMG00920, ATMG00970, ATMG01000, ATMG01010, ATMG01020, ATMG01030, ATMG01040, ATMG01050, ATMG01060, ATMG01090, ATMG01100, ATMG01130, ATMG01140, ATMG01150, ATMG01180, ATMG01200, ATMG01210, ATMG01230, ATMG01240, ATMG01260, ATMG01290, ATMG01300, ATMG01310, ATMG01350, ATMG01370, and ATMG01400. Such POFs can be analyzed (e.g., knock-out mutation, over-expression; etc.) for their ability to modify the amount of at least one biochemical component in the plant species in which it was found, i.e., *Arabidopsis* for the POFs identified above. After it has been determined that a POF can modify the amount of at least one biochemical component in the plant species in which it was found, the POF can be introduced (e.g., in accordance with the methods described herein and known in the art) into another plant species, which is preferably from another genus and the WT of which does not contain the POF, and analyzed for its ability to modify the amount of at least one biochemical component in that plant species. When the protein database was searched with a protein query using the NCBI BLAST program, QQS had an Expect value of 4e-29 to itself only as determined using the method of compositional matrix adjust.

EXAMPLES

The following examples serve to illustrate the present disclosure. The examples are not intended to limit the scope of the claimed invention.

Example 1

This example describes the construction of a vector for expression of QQS in plants other than *Arabidopsis*.

Figure 3:
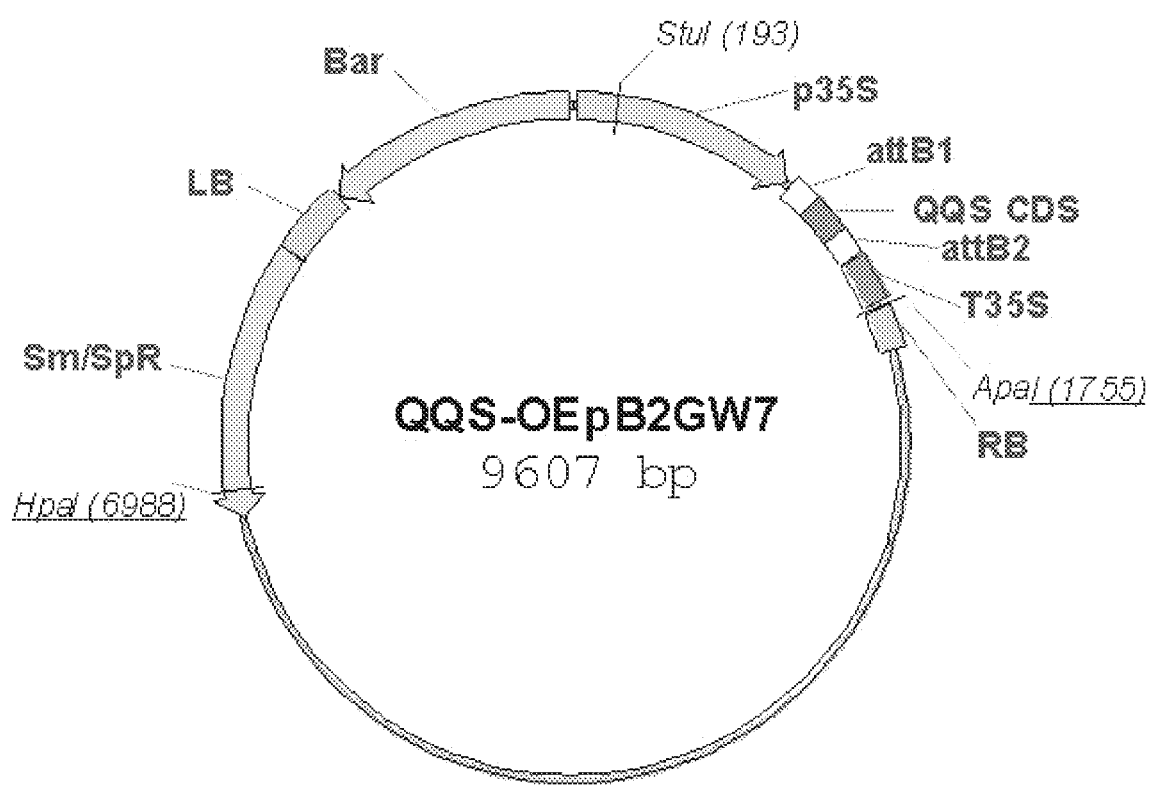
FIG. 3 is a drawing of the construction of a vector (QQS-OE At3g30720) for expression of QQS in plants other than *Arabidopsis*, wherein Hpa I, Stu I and Apa I are restriction endonuclease sites, Sm/SpR is a gene resistant to spectinomycin, LB is the left transfer-DNA border, Bar is a gene that confers resistance to the herbicide bialaphos, p35S is the Cauliflower mosaic virus (CaMV) 35S promoter, attB1 and attB2 are Gateway DNA recombination sites B1 and B2, T35S is the terminator of the CaMV 35S promoter, RB is the right transfer-DNA border, and QQS CDS is the coding sequence for QQS (180 nts; nucleotides 301-480 of SEQ ID NO: 1).

A 35S::QQS fusion construct was made by cloning the amplified, full-length, coding sequence into a binary vector pB2GW7 as shown in FIG. 3. QQS was expressed under the control of the 35S promoter. 35S::QQS-pB2GW7 vector was transformed into *Agrobacterium tumefaciens* strain EHA101.

Example 2

This example describes the transformation and selection of transgenic, QQS-expressing soybean lines.

The cultivar Williams 82 was transformed by *Agrobacterium*-mediated transformation using the half-seed explants method (Paz et al., Euphytica 136: 167-179 (2004)). The transformation and selection of R1 plants were performed in the Plant Transformation Facility at Iowa State University. Soybean plants from independent transformations were selected based on Bar resistance.

Example 3

This example describes the analysis of starch content of the leaves of soybean expressing QQS as compared to WT soybean.

Transgenic, QQS-expressing soybean lines (ST94-32#1, ST94-32#2 and ST94-16#1) and a WT soybean line (Williams 82) were grown in pots with three plants/pot under controlled environmental conditions of 16 hours of light at 27° C. and 8 hours of dark at 20° C. in a growth chamber. The pots were placed randomly in the growth chamber.

Leaves from the top nodes of three individual plants (500-1,000 mg fresh weight) were pooled and boiled in 50 mL 80% (v/v) ethanol. The boiled leaves were then ground with a mortar and pestle in 80% ethanol and centrifuged for 10 min at 13,000 rpm. The resulting pellet was washed twice with 80% ethanol. After washing, the insoluble material was suspended in 10 mL of distilled water and boiled for 30 min. Total starch (D-glucose) in each leaf sample was quantified using amyloglucosidase and Megazyme's GOPOD format (Megazyme International Ireland Ltd., Wicklow, Ireland). This analysis was conducted in triplicate. The results are shown in Table 1 and FIG. 2.

Example 4

This example describes the analysis of oil, protein and moisture contents of the seeds of soybean expressing QQS as compared to WT soybean.

The oil, protein, and moisture contents of seeds were measured by nuclear magnetic resonance (NMR) with the Minispec-mq-one (BRUKER Optics Inc., The Woodlands, Tex.). Seeds were placed in a 10 mm glass tube and weighed. The tube was placed in the Minispec-mq-one and on-screen instructions were followed. The software provided with the Minispec-mq-one calculates the % of oil, protein, and moisture as desired. Data were transformed from fresh weight to dry weight. The results are shown in Table 1 and FIG. 2.

Example 5

This example describes the analysis of total RNA of the leaves of soybean expressing QQS as compared to WT soybean.

Total RNA was extracted from the pooled leaf samples of Example 1 using the TRIzol RNA isolation method. Total RNA was purified using the QIAGEN RNeasy Mini Kit (QIAGEN, Valencia, Calif.).

One microgram of total RNA was reverse-transcribed using 200 ng random hexamers (Invitrogen, Paisley, UK) and Superscript II reverse transcriptase (Invitrogen) according to the supplier's instructions. cDNA was stored at 4° C. until amplified using polymerase chain reaction (PCR).

Specific primers and fluorogenic probes for QQS were purchased from Applied Biosystems (At03403756_sH UBQ10; Warrington, UK) for use in PCR. The 18S ribosomal RNA (18S rRNA) control Reagent (Applied Biosystems) was used as an endogenous control to normalize for differences in the amount of total RNA in each sample and for RNA quality control (Zhong et al., Biochem. Biophys. Res. Comm. 259: 523-526 (1999); Schmittgen et al., J. Biochem. Biophys. Meth. 46: 69-81 (2000); and Bhatia et al., Anal. Biochem. 216: 223-226 (1994)). PCR reactions were performed using the 7500 Fast Real-Time PCR System (Applied Biosystems). Each reaction was performed in 25 μl reactions and contained the equivalent of 5 ng of reverse-transcribed RNA (1 ng RNA for the 18S analyses), 50% TaqMan 2× PCR Master Mix (PE Applied Biosystems), and 1.25 μl of primer/probe mix as recommended by the manufacturer. Conditions for the PCR reaction were 10 min at 95° C. and then 40 cycles, each consisting of 15 sec at 95° C., and 1 min at 60° C.

The relative RNA levels within the samples were determined by generating standard curves for the PCR reaction by using the cDNA from one sample and making 2-fold serial dilutions covering the range equivalent to 100 ng-3.125 ng of total RNA (for 18S rRNA analyses, the range was 4 ng-0.125 ng). Samples were analysed using the standard curve method described by Applied Biosystems. Those samples, which showed more than 2 cycle threshold (Ct) variation from the median 18S rRNA Ct value, were excluded so that expression profiles were not distorted. The results are shown in Table 1.

TABLE 1

| Sample | QQS/18S rRNA (by RT-PCR) | Starch (mg/g fresh wt; % decrease) | Oil (% of dry wt; % decrease) | Protein (% of dry wt; % increase) | Fresh Weight (mean g per seed) |
|---|---|---|---|---|---|
| QQS-Williams 82 #1 | 81.78 | 4.64*; 70.18% | 19.05*; 5.00% | 51.24**; 60.63% | 0.162 |
| QQS-Williams 82 #2 | 4.57 | 2.71*; 82.58% | 16.76**; 16.41% | 42.31**; 32.63% | 0.161 |
| QQS-Williams 82 #11 | 15.81 | 7.51*; 51.74% | 17.39**; 13.27% | 46.92**; 47.08% | 0.156 |
| Williams 82 | 0.00 | 15.56 | 20.05 | 31.9 | 0.159 |

*Student's t-test, P < 0.05
**Student's t-test, P < 0.01

As shown in Table 1 and FIG. 2, the starch content of leaves of soybean lines expressing QQS is significantly lower than the starch content of leaves of WT soybean (Williams 82). The oil content of seeds of QQS-expressing soybean is also lower than the oil content of seeds of WT soybean. In distinct contrast to the starch content of leaves and the oil content of seeds, however, the protein content of seeds of QQS-expressing soybean is significantly higher than the protein content of seeds of WT soybean.

Example 6

This example describes the analysis of oil, protein and moisture contents of the seeds of soybean expressing QQS as compared to WT soybean and grown in a growth chamber, a greenhouse, or a field.

Transgenic, QQS-expressing soybean lines (ST94-32#1, ST94-32#2 and ST94-16#1) and a WT soybean line (Williams 82) were grown in pots with three plants/pot under controlled environmental conditions of 16 hours of light at 27° C. and 8 hours of dark at 20° C. in a growth chamber. The pots were placed randomly in the growth chamber.

Transgenic, QQS-expressing soybean lines (ST94-32#1, ST94-32#2 and ST94-16#1) and a WT soybean line (Williams 82) were grown in pots with three plants/pot under controlled environmental conditions of 16 hours of light at 27° C. and 8 hours of dark at 20° C. in a greenhouse. The pots were placed randomly in the greenhouse.

Transgenic, QQS-expressing soybean lines (ST94-32#1, ST94-32#2 and ST94-16#1) and a WT soybean line (Williams 82) were grown in a field in Ames, Iowa Five replicates, each containing one row of each line, were planted.

The oil, protein, and moisture contents of seeds were measured by near-infrared spectroscopy (NIRS). Data were adjusted to a moisture content of 10.97%. The data are shown in Tables 2-4. As shown in Table 2, protein is increased (up to 16.85%) and oil and fiber are decreased in QQS-expressing mutant soybean plants grown in a growth chamber. As shown in Table 3, protein is increased (up to 13.5%), and oil, fiber and carbohydrates are decreased in QQS-expressing mutant soybean plants grown in a green house. As shown in Table 4, protein is increased (up to 9.5%), and oil, fiber and carbohydrates are decreased in QQS-expressing mutant soybean plants grown in a field.

TABLE 2

Growth Chamber Data for R2 Seeds (Year 2010)

| | Mean | | | | | Change (% WT) | | | | QQS | Leaf |
| --- | --- | --- | --- | --- | --- | --- | --- | --- | --- | --- | --- |
| | Moisture (%) | Protein* | Oil* | Fiber* | P + O* | Protein | Oil | Fiber | P + O | Transcripts+ | Starch^ |
| QQS-Williams 82 #1 | 7.83 | 38.47 | 18.49 | 4.88 | 56.96 | 9.93 | −5.25 | −4.72 | 4.49 | 81.7844 | 4.6401 |
| QQS-Williams 82 #2 | 6.57 | 39.33 | 18.18 | 4.81 | 57.51 | 12.37 | −6.81 | −6.06 | 5.51 | 5.11354 | 5.2615 |
| QQS-Williams 82 #3 | 5.93 | 40.90 | 17.57 | 4.78 | 58.47 | 16.85 | −9.96 | −6.72 | 7.26 | 2.73198 | 13.638 |
| QQS-Williams 82 #4 | 6.93 | 37.90 | 18.73 | 4.81 | 56.62 | 8.28 | −4.01 | −6.06 | 3.88 | 45.3269 | 14.94 |
| QQS-Williams 82 #5 | 5.97 | 37.56 | 18.73 | 4.88 | 56.28 | 7.30 | −4.01 | −4.73 | 3.25 | 4.57207 | 2.7128 |
| QQS-Williams 82 #6 | 6.40 | 39.54 | 17.98 | 4.74 | 57.51 | 12.96 | −7.86 | −7.39 | 5.51 | 2.62104 | 5.7704 |
| QQS-Williams 82 #7 | 7.50 | 38.89 | 18.32 | 4.78 | 57.20 | 11.11 | −6.11 | −6.73 | 4.94 | 2.87029 | 11.014 |
| QQS-Williams 82 #8 | 10.97 | 40.01 | 19.07 | 4.57 | 59.08 | 14.32 | −2.27 | −10.72 | 8.38 | 2.19775 | 5.6369 |
| Williams 82 | 6.73 | 35.00 | 19.51 | 5.12 | 54.51 | 0.00 | 0.00 | 0.00 | 0.00 | 0 | 15.561 |

*data shown for mean protein, oil, fiber, and P + O (protein and oil) are based on % of dry weight
+data shown for QQS transcripts are based on QQS/18S rRNA
^data shown for leaf starch are based on mg/g fresh weight

TABLE 3

Green House Data for R2 Seeds (Year 2011)

| | Mean | | | | | | Change (% WT) | | | | | QQS | Leaf |
| --- | --- | --- | --- | --- | --- | --- | --- | --- | --- | --- | --- | --- | --- |
| | Moisture (%) | Protein* | Oil* | Fiber* | CHO* | P + O* | Protein | Oil | Fiber | CHO | P + O | Transcripts+ | Starch^ |
| QQS-Williams 82 #10 Plant 4 | 7.30 | 40.57 | 20.35 | 4.54 | 19.83 | 60.92 | 10.39 | −2.35 | −7.04 | −13.06 | 5.78 | 0.745933 | |
| QQS-Williams 82 #10 Plant 8 | 7.20 | 39.25 | 19.63 | 4.75 | 21.67 | 58.88 | 6.80 | −5.84 | −2.78 | −5.00 | 2.23 | 0.745933 | |
| QQS-Williams 82 #1 | 7.70 | 41.72 | 18.24 | 4.65 | 20.70 | 59.95 | 13.51 | −12.51 | −4.92 | −9.26 | 4.09 | 81.78443 | 4.64013 |
| QQS-Williams 82 #1 Plant 5 | 7.10 | 39.49 | 20.04 | 4.68 | 21.53 | 59.08 | 6.24 | −3.85 | −4.20 | −5.61 | 2.59 | 81.78443 | 4.64013 |

TABLE 3-continued

Green House Data for R2 Seeds (Year 2011)

| | Mean | | | | | | Change (% WT) | | | | | QQS Transcripts[+] | Leaf Starch[^] |
|---|---|---|---|---|---|---|---|---|---|---|---|---|---|
| | Moisture (%) | Protein* | Oil* | Fiber* | CHO* | P + O* | Protein | Oil | Fiber | CHO | P + O | | |
| QQS-Williams 82 #4 | 7.47 | 39.74 | 18.34 | 4.82 | 22.40 | 58.08 | 8.12 | −12.00 | −1.36 | −1.81 | 0.84 | 45.32694 | 14.9403 |
| QQS-Williams 82 #5 | 10.90 | 39.49 | 19.00 | 4.89 | 21.91 | 58.49 | 7.46 | −8.84 | 0.06 | −3.94 | 1.56 | 4.572071 | 2.71278 |
| QQS-Williams 82 #2 Plant 1 | 9.17 | 38.94 | 18.93 | 4.82 | 22.61 | 57.87 | 5.95 | −9.17 | −1.36 | −0.90 | 0.48 | 2.621037 | 5.77036 |
| QQS-Williams 82 #3 | 7.70 | 38.08 | 20.04 | 4.819 | 22.363 | 58.12 | 3.6 | −3.9 | −1.4 | −2.0 | 0.9 | 2.870293 | 11.014 |
| Williams 82 #5 | 7.60 | 40.01 | 19.244 | 4.681 | 21.359 | 59.26 | 8.9 | −7.7 | −4.2 | −6.4 | 2.9 | 2.197754 | 5.63693 |
| Williams 82 | 9.43 | 36.75 | 20.84 | 4.89 | 22.82 | 57.59 | 0.00 | 0.00 | 0.00 | 0.00 | 0.00 | 0 | 15.5605 |

*data shown for mean protein, oil, fiber, CHO (carbohydrates), and P + O (protein and oil) are based on % of dry weight
[+]data shown for QQS transcripts are based on QQS/18S rRNA
[^]data shown for leaf starch are based on mg/g fresh weight

TABLE 4

Field Data for R2/R3 Seeds (Year 2011)

| | Mean | | | | | | Change (% WT) | | | | | QQS Transcripts[+] | Leaf Starch[^] |
|---|---|---|---|---|---|---|---|---|---|---|---|---|---|
| | Moisture (%) | Protein* | Oil* | Fiber* | CHO* | P + O* | Protein | Oil | Fiber | CHO | P + O | | |
| QQS-Williams 82 #1 | 8.5 | 35.99 | 17.91 | 5.15 | 24.87 | 53.90 | 3.33 | −0.57 | −1.95 | −3.70 | 2.00 | 81.78443 | 4.64013 |
| QQS-Williams 82 #6 | 9.7 | 36.98 | 17.19 | 5.08 | 24.66 | 54.17 | 6.17 | −4.55 | −3.25 | −4.49 | 2.52 | 2.621037 | 5.77036 |
| QQS-Williams 82 #7 | 7.0 | 35.78 | 17.91 | 5.12 | 25.11 | 53.69 | 2.74 | −0.57 | −2.60 | −2.77 | 1.61 | 2.870293 | 11.014 |
| QQS-Williams 82 #9 | 7.3 | 38.17 | 16.20 | 5.05 | 24.49 | 54.37 | 9.50 | −10.23 | −3.90 | −4.89 | 2.78 | 0.031645 | 8.73995 |
| Williams 82 | 7 | 34.83 | 18.01 | 5.25 | 25.82 | 52.84 | 0.00 | 0.00 | 0.00 | 0.00 | 0.00 | 0 | 15.5605 |

*data shown for mean protein, oil, fiber, CHO (carbohydrates), and P + O (protein and oil) are based on % of dry weight
[+]data shown for QQS transcripts are based on QQS/18S rRNA
[^]data shown for leaf starch are based on mg/g fresh weight While protein content and total protein+oil content increased under all conditions, the increases in protein content and total protein+oil content were greater under growth chamber/green house conditions compared to field conditions. The differences may reflect the fact that the soil in the growth chamber and the green house was supplemented with fertilizer (i.e., Miracle Gro Excel 15-5-15), whereas the soil in the field was not. This study will be repeated with supplementation of soil under all growth conditions.

All references, including publications, patent applications, and patents, cited herein are hereby incorporated by reference to the same extent as if each reference were individually and specifically indicated to be incorporated by reference and were set forth in its entirety herein.

The use of the terms "a," "an," "the," and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to illuminate better the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. It should be understood that the illustrated embodiments are exemplary only, and should not be taken as limiting the scope of the invention.

What is claimed is:

1. A method of producing a food product with increased protein content comprising:
   (a) obtaining a transgenic plant or a transgenic part thereof, wherein the transgenic plant or the transgenic part thereof is transformed with a polynucleotide, which encodes an *Arabidopsis* Qua-Quine Starch (QQS) polypeptide, operably linked to a non-native promoter that expresses the QQS polypeptide in the transgenic plant or the transgenic part thereof;
   (b) selecting the transgenic plant or the transgenic part thereof with increased total protein content compared to the total protein content in a corresponding wild-type (WT) plant or a corresponding WT part thereof that does not comprise and express the polynucleotide, which encodes the *Arabidopsis* QQS polypeptide, operably linked to the non-native promoter; and
   (c) preparing the food product from the transgenic plant or the transgenic part thereof with increased total protein content,
   whereupon the food product with increased protein content is produced.

2. The method of claim 1, wherein the transgenic plant is a crop plant.

3. The method of claim 2, wherein the crop plant is a cereal crop.

4. The method of claim 3, wherein the cereal crop is corn.

5. The method of claim 3, wherein the cereal crop is rice.

6. The method of claim 2, wherein the crop plant is soybean.

* * * * *

SEQUENCE LISTING

<160> NUMBER OF SEQ ID NOS: 2

<210> SEQ ID NO 1
<211> LENGTH: 586
<212> TYPE: DNA
<213> ORGANISM: Arabidopsis thaliana QQS

<400> SEQUENCE: 1

```
ctcagaagaa gcctcctttc gatctgtcag ccattgaaga aacctccttt cgatctgtca      60
gccattgaag atcagaagaa acaagactca cacggtcagc cattgaagaa gcctcctctc     120
attacctctc atcaaacatc tagatctgta cccaaacctt atcccttttt ccttatttct     180
cgctttgtct attcttaatc tgattaatac ttgttgttgt tccaggttat agaagatctg     240
ggttgtgtta tatgcttcat tttctccaca gcgaccagtt ggtgtttggt tcttagattc     300
atgaagacca atagagagca ggaaatttac gttgaaagaa gcttcaaacc aaacaattca     360
acaattcaga atttgatgga cattgaaagg ttcattttgc ctcacacttc tacatcaggt     420
gtcgcaaggc tcaaaatgag ggtcatatca tgggtcgggc ttcagttcta caactactga     480
tattgggcct tatcacaaat tagttatagg gccattgtat ccaatattta atatctctgt     540
aaacttgttt aatggttatt ttgttctaat gcccattaca actaga                    586
```

<210> SEQ ID NO 2
<211> LENGTH: 59
<212> TYPE: PRT
<213> ORGANISM: Arabidopsis thaliana QQS

<400> SEQUENCE: 2

```
Met Lys Thr Asn Arg Glu Gln Glu Ile Tyr Val Glu Arg Ser Phe Lys
1               5                   10                  15

Pro Asn Asn Ser Thr Ile Gln Asn Leu Met Asp Ile Glu Arg Phe Ile
            20                  25                  30

Leu Pro His Thr Ser Thr Ser Gly Val Ala Arg Leu Lys Met Arg Val
        35                  40                  45

Ile Ser Trp Val Gly Leu Gln Phe Tyr Asn Tyr
    50                  55
```